US006989272B1

(12) United States Patent
Savion et al.

(10) Patent No.: US 6,989,272 B1
(45) Date of Patent: Jan. 24, 2006

(54) APPARATUS AND METHOD FOR PROCESSING AND TESTING A BIOLOGICAL SPECIMEN

(75) Inventors: Naphtali Savion, Givat Shmuel (IL); Doron Lindner, Haifa (IL)

(73) Assignees: David Varon, Kfar Bilu A (IL); Ramot at Tel-Aviv University Ltd., Tel Aviv (IL)

( * ) Notice: Subject to any disclaimer, the term of this patent is extended or adjusted under 35 U.S.C. 154(b) by 578 days.

(21) Appl. No.: 09/799,355

(22) Filed: Mar. 6, 2001

(51) Int. Cl.
*G01N 21/13* (2006.01)

(52) U.S. Cl. .................. 436/46; 436/47; 436/164; 422/63; 422/67; 422/82.05

(58) Field of Classification Search ............ 422/63–67, 422/82.05; 436/43, 44, 46, 47, 48, 164, 174, 436/180
See application file for complete search history.

(56) References Cited

U.S. PATENT DOCUMENTS

| 3,687,632 | A | | 8/1972 | Natelson |
| 3,826,622 | A | | 7/1974 | Natelson |
| 4,908,320 | A | * | 3/1990 | Zakowski et al. ............ 436/45 |
| 5,365,084 | A | | 11/1994 | Cochran et al. |
| 5,523,238 | A | | 6/1996 | Varon et al. |
| 5,730,697 | A | | 3/1998 | Auchinleck |
| 5,783,446 | A | * | 7/1998 | Saul et al. ..................... 436/45 |
| 5,856,194 | A | | 1/1999 | Arnquist et al. |
| 6,225,126 | B1 | * | 5/2001 | Cohen et al. ................. 436/69 |
| 2004/0128874 | A1 | | 7/2004 | Sakai et al. |

FOREIGN PATENT DOCUMENTS

| DE | 35 22 098 A1 | 1/1987 |
| EP | 0 337 300 A2 | 10/1989 |
| EP | 0 828 822 A2 | 6/1994 |

* cited by examiner

*Primary Examiner*—Jeffrey R. Snay
(74) *Attorney, Agent, or Firm*—Browdy and Neimark, PLLC

(57) ABSTRACT

A device for analyzing liquid body-specimens, the device comprising at least one specimen handling station for obtaining preparation on a carrying media, and an imaging station fitted with an optical image capturing device for analyzing the preparation. A carriage with a carrying media receptacle rotatably retains the carrying media and is displaceable between a loading position and an unloading position with respective positions at the stations. An incremental displacement mechanism for displacing at least one of the carrying media and an imaging device so as to obtain at least one consecutive image of the preparation.

42 Claims, 18 Drawing Sheets

APPARATUS AND METHOD FOR PROCESSING AND TESTING A BIOLOGICAL SPECIMEN

FIELD OF THE INVENTION

The present invention relates to an apparatus and method for assaying specimens. In particular, the apparatus and method of the invention are suitable for testing techniques which involve an image analysis or assessment stage, e.g. the method performed using an optical microscope.

BACKGROUND OF THE INVENTION

Assaying of biological specimens is routine laboratory procedure, both in clinical as well as in the research laboratory. Examples of specimens which are routinely tested consist of urine, blood and others. A critical blood parameter which needs to be determined, primarily in hospital emergency rooms and intensive care units, as well as in patients prior to operation, concerns platelet function. U.S. Pat. No. 5,523,238 describes a cone and plate device and method for determining platelet function in a primary hemostasis. In accordance with this method, a blood sample or a platelet containing fraction thereof is introduced into a well-like vessel (plate member) with a flat bottom on which plasma proteins are immobilized. A cone device is then rotated in the vessel and as a result of shear forces which develop on the surface blood platelets adhere and aggregate on the plasma protein coated surface of the plate member. The platelet function can then be determined based on the pattern of adhered aggregated blood platelets.

GENERAL DESCRIPTION OF THE INVENTION

The invention has its purpose of providing an automatic apparatus and method for handling and assaying a biological specimen. The apparatus and method of the invention is useful for handling an analysis of a variety of different specimens, primarily biological specimens. One preferred embodiment of the invention concerns the assaying of blood or a platelet-containing fraction thereof, for the purpose of determining platelet function. However, the invention is not limited to this specific embodiment.

According to a first object of the invention, there is provided a device for analyzing liquid body-specimens, the device comprising at least one specimen handling station for obtaining preparation on a carrying media, and an imaging station fitted with an optical image capturing device for analyzing the preparation; a carriage fitted with a carrying media receptacle retaining the carrying media and being displaceable between a loading position and an unloading position with respective positions at said stations; a controller; and a displacing mechanism for incrementally displacing at least one of said carrying media and an imaging device so as to obtain at least one consecutive image of the preparation. Optionally the controller is programmable such that several examination routines and procedures may be programmed and stored.

By one particular embodiment of the invention, the displacing mechanism is fitted for incremental angular displacement of the plate member (or the imaging device). By still another embodiment, the displacement is fitted for planer displacing about an X-Y type coordination system, and by still an embodiment the displacement is by polar coordination system.

The at least one handling station typically comprises one or more of a mixing or shaking mechanism, a coloring stage, a rinsing stage and a drying station. For assaying the specimen and obtaining the preparation, containers with different dyeing/processing and rinsing liquids are provided with suitable liquid propelling arrangements, e.g. various pumping arrangements. Accordingly, the device further comprises a waste container for collecting refuse liquids as well as refuse carrying media.

The terms mixing and mixing station refer, by a particular application of the invention, to laminar flow formation of the specimen within the carrying media, and to a station of the device for generating said laminar flow, respectively. However, these terms may also refer to mixing, as known per se, depending on the specific application.

By a preferred embodiment of the invention, the carrying media is a well-like member of a cone and plate couple, whereby the well is rotatably engagable with the carriage receptacle, and wherein the cone member is rotatably fixable to the mixing station for rotating within the plate member, while the latter is kept stationary.

According to a particular embodiment of the invention, the drying station comprises a cylindrical plug insatiable into the well with a forehead of the plug being essentially flat and having a diameter snugly receivable within the well; at least one air suction port formed at the forehead and suitable venting inlet to admit air flow towards the forehead; the plug further comprising an axial restricting arrangement for securing a fixed geometry between the forehead of the plug member and a base of the well (plate member).

According to a preferred embodiment of the invention, the device is adapted for capturing several consecutive images of the preparation. For that purpose, once the carrying media with the preparation is introduced into the imaging station, either one or both of the optical device, typically a microscope, is the carrying media, namely the plate member of a cone and plate couple, is angularly displaced for obtaining a plurality of consecutive images of the preparation. For this purpose, it is desirable that the carrying media be positioned offset with respect to the longitudinal axis of the optical device.

For monitoring and controlling rotation and angular displacement of the plate member during the imaging process, it is formed with indicia for communication with corresponding sensors. These indicia may be in accordance with one embodiment, a plurality of marks or, in accordance with another embodiment, a plurality of recesses according to which the sensors are optical-type sensors which detect sequences of light interference or light reflections as the plate member rotates.

The invention is further concerned with providing a cone and plate couple for use in conjunction with an analyzing device in accordance with the present invention. In accordance with this application, the plate member is a well-like shaped member formed with a substantially flat and smooth base surface with a cylindrical wall upwardly extending therefrom. The cone member is formed with a conical forehead and a cylindrical rim portion snugly receivable within the plate member. During a mixing process of the specimen, it is important to retain a fixed geometry between the forehead of the cone member and the base of the plate member. For this purpose, during a mixing process, a tip of the forehead of the cone member engages the base of the plate member. Preferably, at least the base surface of the plate member is transparent or at least translucent. For best results, at least the base surface is made of a uniform-density material, for reducing light fraction and obtaining high quality images.

Preferably both the plate member and the cone member are formed with indicia for communication with corresponding sensors. Typically said indicia are a plurality of recesses or grooves or laterally extending wing members, formed at regular intervals for detection by corresponding optical sensors (light emitting/receiving type sensors).

Still another concern of the invention is a method for analyzing liquid body-specimens, the method comprising the following steps:

(a) Obtaining a liquid body-specimen analyzer comprising at least one specimen handling station for obtaining preparation on a carrying media, an imaging station fitted with an optical image capturing device, a carriage fitted with a carrying media receptacle and being displaceable between a loading position, and an unloading position with respective positions at said stations, and a programmable controller;

(b) engaging the specimen carrying media with the carriage;

(c) Obtaining a specimen of body liquid and introducing it on the specimen carrying media;

(d) displacing the carriage from the loading position to the at least one specimen handling station so as to obtain a preparation;

(e) advancing the carriage to the imaging station and incrementally displacing one of the specimen carrying media and imaging device for obtaining one or more consecutive images of the preparation;

(f) displacing the carriage to the unloading position for disposal of the carrying media.

In accordance with a preferred embodiment of the analyzing method, at the handling station of step (d) the plate member is retained stationary and the cone member is rotated against the plate member for mixing the specimen.

Furthermore, at step (e) the plate member is rotated at regular angular intervals so as to obtain a plurality of consecutive images of the preparation, said images being captured by the optical image capturing device. For that purpose, at step (e) the carrying media is placed offset with respect to a longitudinal axis of the imaging device.

The invention also calls for a kit for use with liquid body-specimen analyzer, the kit comprising:

(a) At least one cone-and-plate couple;
(b) At least one container with a liquid for obtaining a preparation; and
(c) A waster container.

Typically, such a kit further comprises:

(d) An instruction manual;
(e) A set of tubes; and
(f) A tube holder.

BRIEF DESCRIPTION OF THE DRAWINGS

In order to understand the invention and to see how it may be carried out in practice, some specific embodiments of the invention will now be described, by way of non-limiting examples only, with reference to the accompanying drawings, in which.

DETAILED DESCRIPTION OF SOME SPECIFIC EMBODIMENTS

Figure 1:
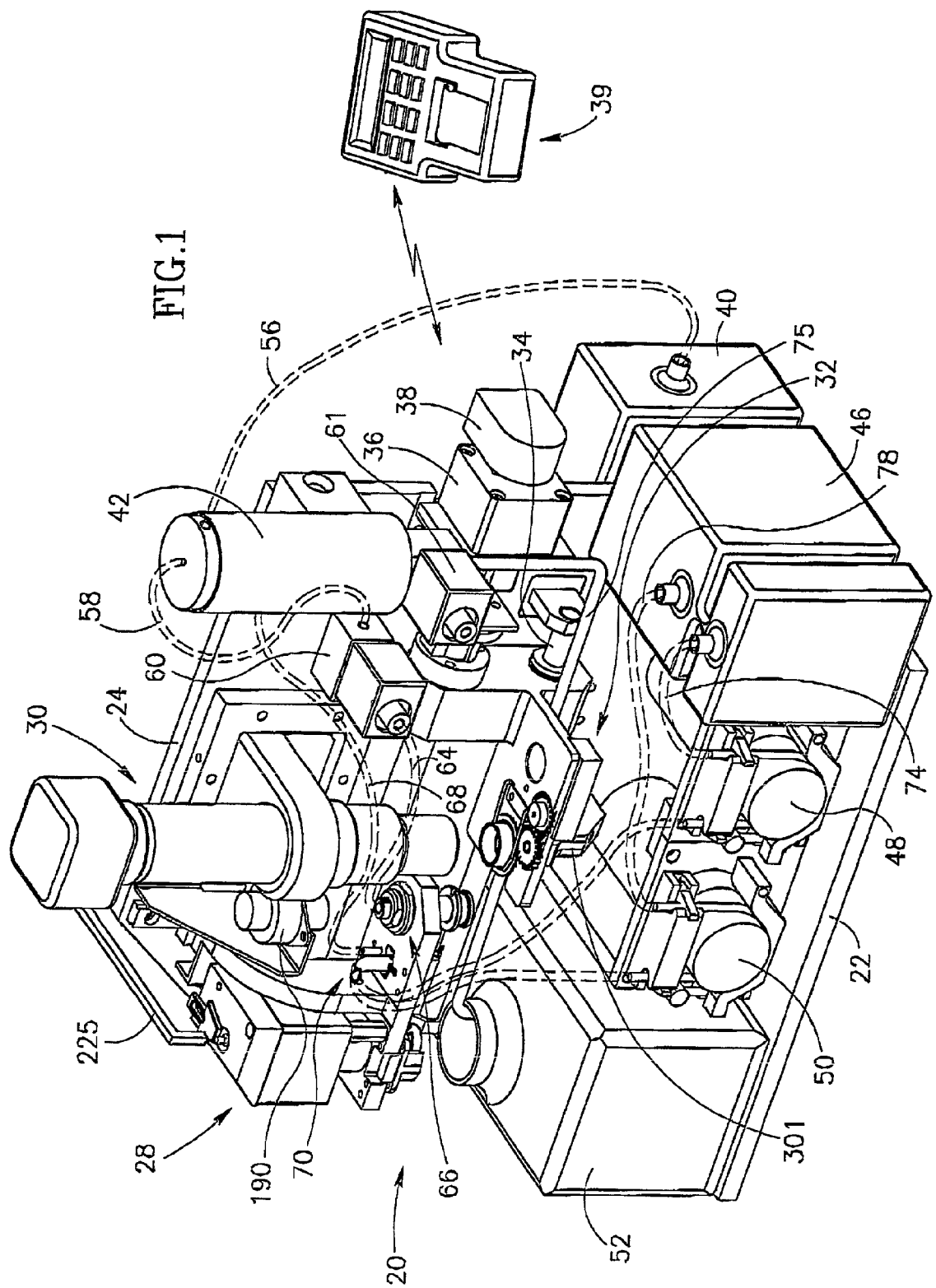
FIG. 1 is an overall view of the analyzing device in accordance with the present invention, the device being installed with liquid containers and a waster container, fitted with suitable tubing; the device illustrated with its carriage member at the imaging station.
Figure 2:
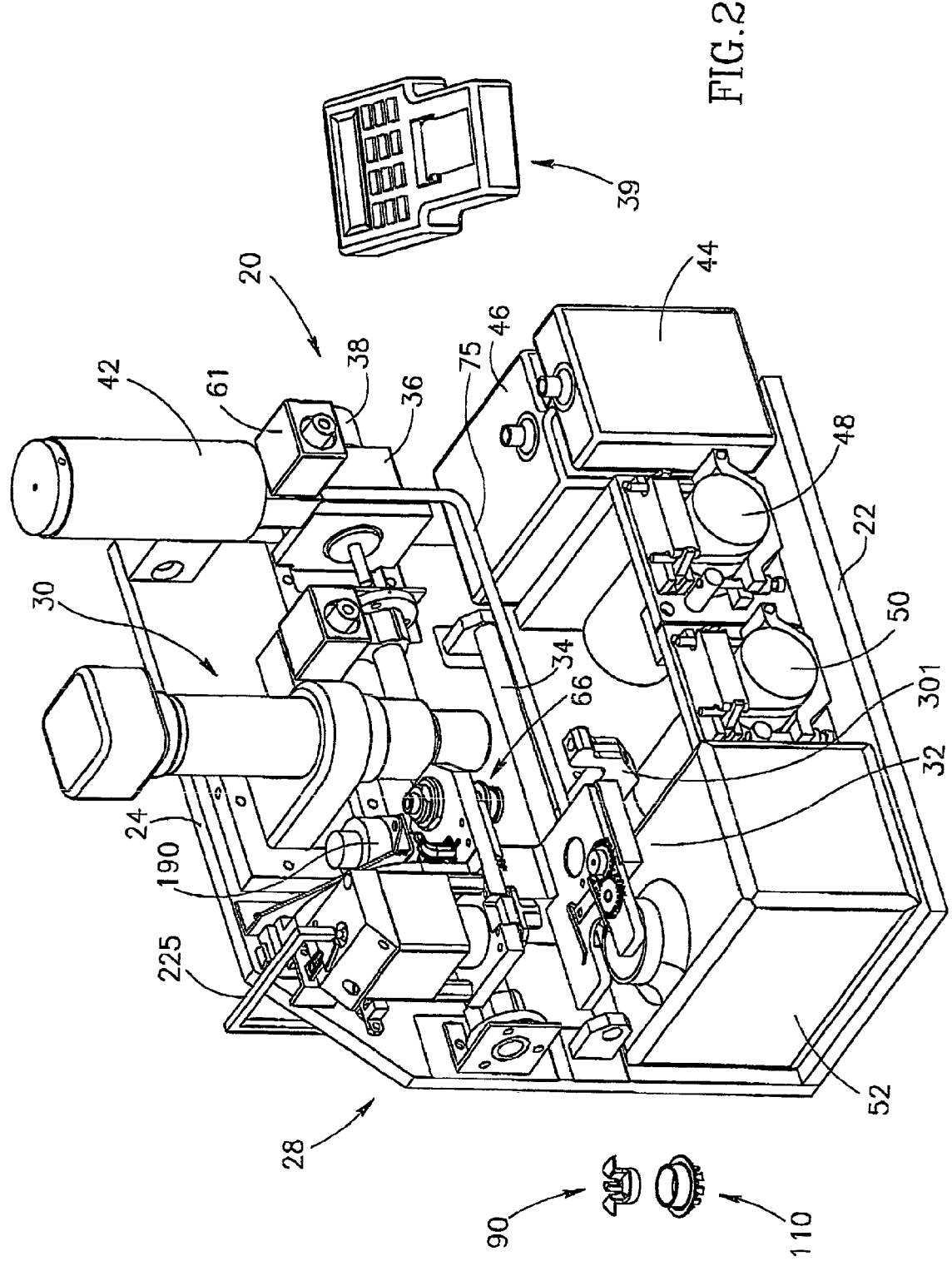
FIG. 2 is an overall view of the device, from a different view, illustrating the device in a standby, loading station, and a plate and cone couple, for use in conjunction therewith.

Attention is first detected in FIGS. 1 and 2 of the drawings illustrating the analyzing device of the present invention at two respective views for visualizing various components of the device generally designated 20. The device is assembled on a support construction comprising a base plate 22 and a rear plate 24 to which the various components of the device are attached. For the sake of clarify a cover of the device is removed. The device comprises several main sub-assemblies, namely a specimen handling assembly generally designated 28, an imaging station 30, a carriage 32 displacingly mounted on a horizontal leading rail and being displaceable therealong by means of motor 36 fitted with an encoder 38.

A controller 39 fitted with a processor, a keypad, a display and a printer is provided, which is either fixed to the device or a portable device (wire or wireless communication with the device). Function of the controller will be discussed in somewhat more detail hereinafter. Typically but not necessary so, the controller is programmable such that several examination routines and procedures may be programmed and stored.

The device further comprises a suction pump 40, a vacuum container 42, a dyeing agent container 44, a rinsing liquid container 46, a dyeing agent pump 48, a rinsing liquid pump 50 and a waste container 52.

For the sake of clarity, flexible tubing extending between the various components is illustrated in dashed lines and is represented only in FIG. 1. A first tube 56 extends between vacuum pump 40 and vacuum container 42. Another tube 58 extends between the vacuum container 42 and a three-way valve member 60, from which one tube 64 extends to a drying assembly 66 and another tube identified as 68 leads to a coloring and rinsing station 70. Three way valve 60 may be replaced by other control valve means, as known per se. Dyeing agent is drawn from a container 44 by means of a tube 74 extending through peristaltic pump 48 and then extends to the coloring and rinsing station 70. Rinsing liquid is transferred to the coloring and rinsing station 70 by means of tube 78 extending through peristaltic pump 50. A waste disposal tube 75 extends between the vacuum container 42 and waste container 52. This tube, according to an embodiment of the invention, is a fixed, rigid tube. Tubes 74 and 78 are flexible, disposable tubes, which are periodically replaced. Other tubes are periodically replaced, as may be required.

It is to be appreciated that the various components of the device, e.g. pumps, sensors, motors, imaging and capturing device, are connected to the controller 39, the latter receiving all input data and issuing responsive control signals. Communication with the controller 39 may be by wire or wireless. Alternatively, the controller may be integrally mounted on the device with suitable wiring.

Figure 3A:
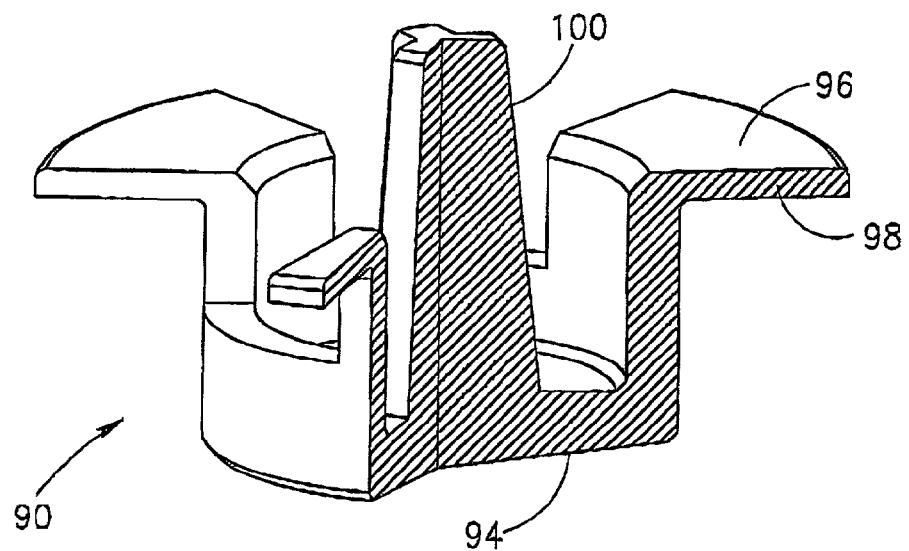
FIG. 3A is a partially sectional isometric view of a cone member of a cone and plate couple, for use in conjunction with an analyzing device of the present invention.
Figure 3B:
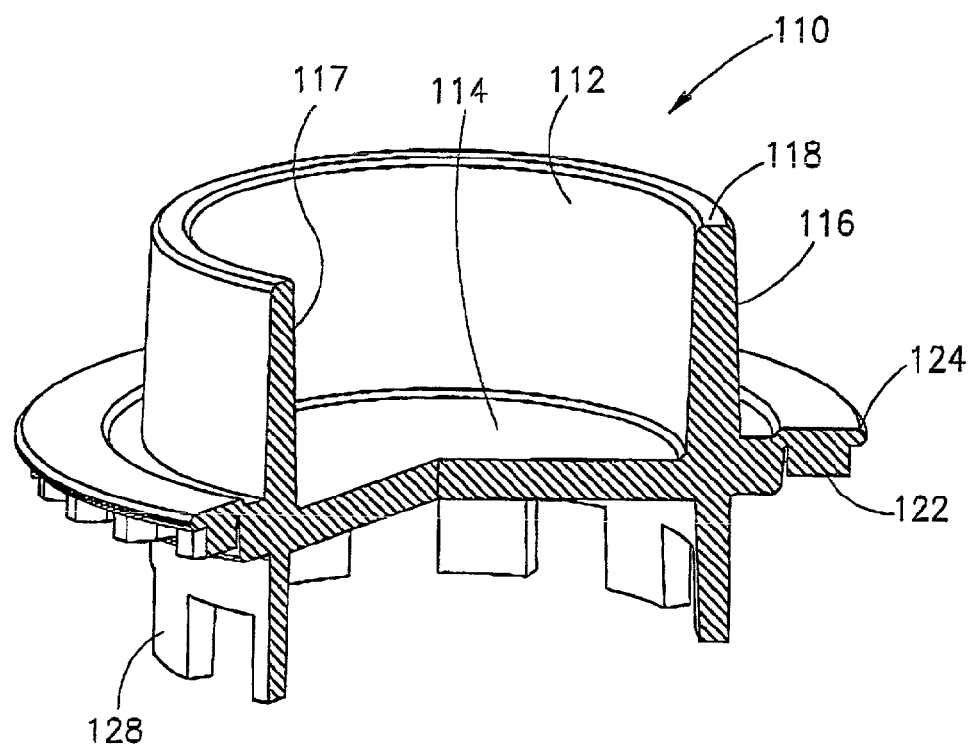
FIG. 3B is a partially sectioned isometric view of a plate member of a cone and plate couple, for use in conjunction with an analyzing device of the invention.

Prior to providing further detailed explanations concerning the analyzing device of the present invention, further reference will be now directed to FIGS. 3A and 3B for illustrating the structure of a cone and plate couple adapted for use with the device 20 in accordance with the present invention. FIG. 3A illustrates the cone member generally designated 90, having a generally cylindrical shape with cylindric side walls 92 and a forehead 94 tapering at an angle of about 2½°. Laterally extending from the top of wall 92 there is a skirt portion 96 which in the present embodiment is divided into three sectors, the purpose of which will become apparent hereinafter. However, it is noted that a bottom surface 98 of said skirt portion is essentially flat and smooth. As can further be seen in FIG. 3A, the cone member comprises a coaxially extending stem 100 having a tapering cross-section for engagement with a chuck at the mixing station 28 as will become apparent hereinafter.

A plate member generally designated 110, illustrated in FIG. 3, has a well-like portion 112 with an essentially smooth and flat base surface 114, from which upwardly extends a cylindrical wall 116 having an upright inner-wall 117, terminating at smooth and flat edge 118. A laterally extending geared rim 122 is concealed by a lateral skirt 124, said geared rim 122 adapted for engagement with a rotation mechanism fitted on the carriage 32 as will become apparent hereinafter. Preferably, at least the base surface 114 of the plate member 110, is transparent or at least translucent. Base surface 114 is essentially parallel to the lateral skirt 124, such that when the plate member is received at the imaging station, the base surface extends normal to a longitudinal axis of the imaging device i.e., to the line of sight thereof, so that images obtained are in focus, also after the plate member is rotated.

Formed at a lower end of the plate member 110 there is a crown-like recessed portion 128 adapted for cooperation with an optical sensor fitted at the carriage 32, as will become apparent hereinafter.

Whilst the particular device described in the present embodiment and the specimen carrying media disclosed in the specification refer in particular to a cone and plate couple, it is to be appreciated that other types of specimen carrying medium may be used with necessary arrangements being made at the analyzing device, *Mutatis mutandis*.

Figure 4B:
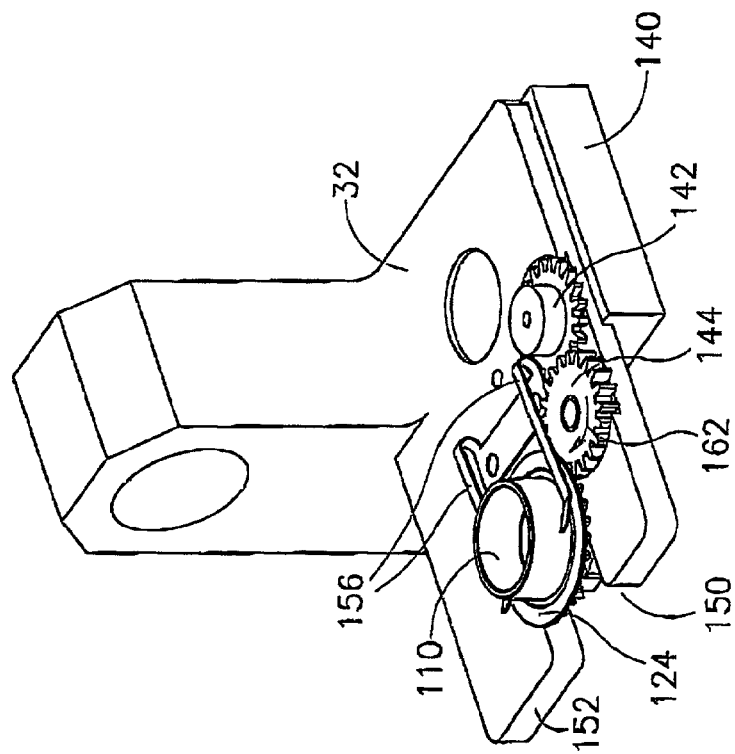
FIG. 4B illustrates the carriage of FIG. 4A with a plate member received thereby.
Figure 4A:
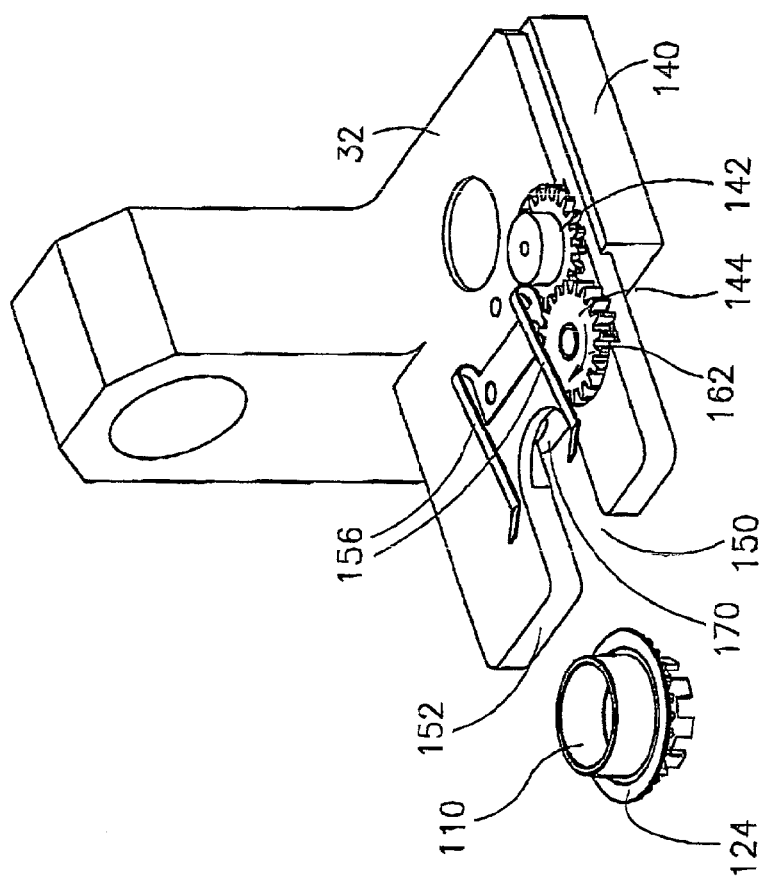
FIG. 4A is an isolation of the carriage and a plate member for use in conjunction with the analyzing device of the invention.
Figure 4C:
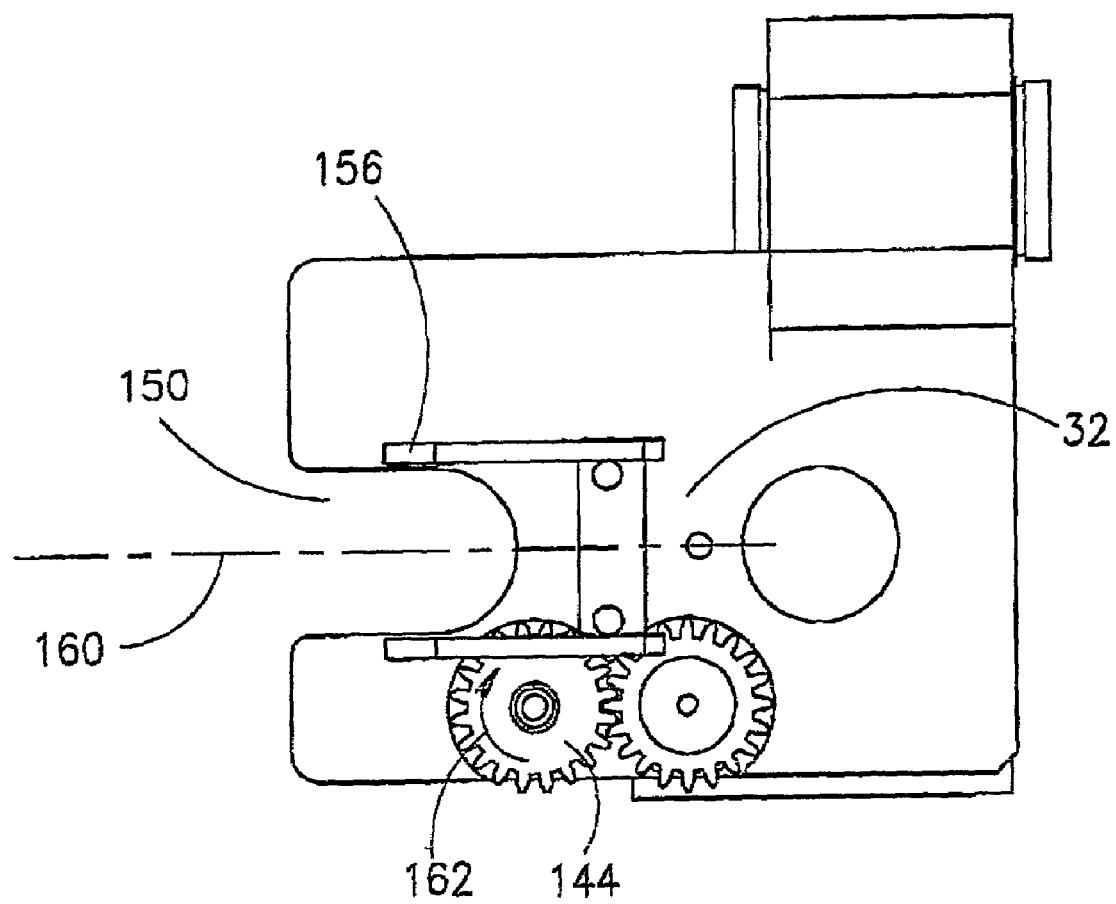
FIG. 4C is a partial top elevation of the carriage, without a plate member.

With further reference to the FIGS. 4A–4C, it is noticeable that the carriage 32 is fitted with a flat motor unit 140 (a flat motor in the present example) rotating an output pinion 142 engaged with a transmission gear 144.

Carriage 32 comprises a carrying media receptacle 150 which in the present embodiment is a U-shaped aperture formed in the carriage 32, with the arms of the U-like shape extending to an end 152 of the carriage. The carriage is also fitted with a pair of springy retention arms 156 for gripping annular skirt 124 of plate member 110, as illustrated in FIG. 4B.

As can be seen best in FIG. 4C, the transmission gear 144 extends into the receptacle 150 at the circular portion thereof, at a location which is offset from center line 160. The location of the transmission gear 144 and its rotation in the direction of arrow 162 ensure that the plate member 110 is biased to an inward position as in FIG. 4B, to a fixed location within the receptacle 150.

As further seen in FIG. 4A, the carriage 32 is fitted at a bottom face thereof with an optical sensor 170 which when the plate member 110 is received in the receptacle 150, as in FIG. 4B, the sensor is capable of detecting and monitoring angular displacement of the plate member 110. The sensor 170 is of the type provided with a light source and a light sensitive device which detects the recesses formed in the crown-like bottom portion 128 (FIG. 3B) of the plate member 110 and by means of the controller 39 connected to the sensor, the precise angular displacement of the plate member 110 over the carriage 32 may be derived.

Referring now back to FIGS. 1 and 2, the carriage 32 is displaceable about the horizontal rod 34 by means of motor 36 and encoder 38 for precise displacement of the carriage and location thereof at each of the respective stations, and it is thus apparent that encoder 38 is connected to the controller 39.

Figure 5A:
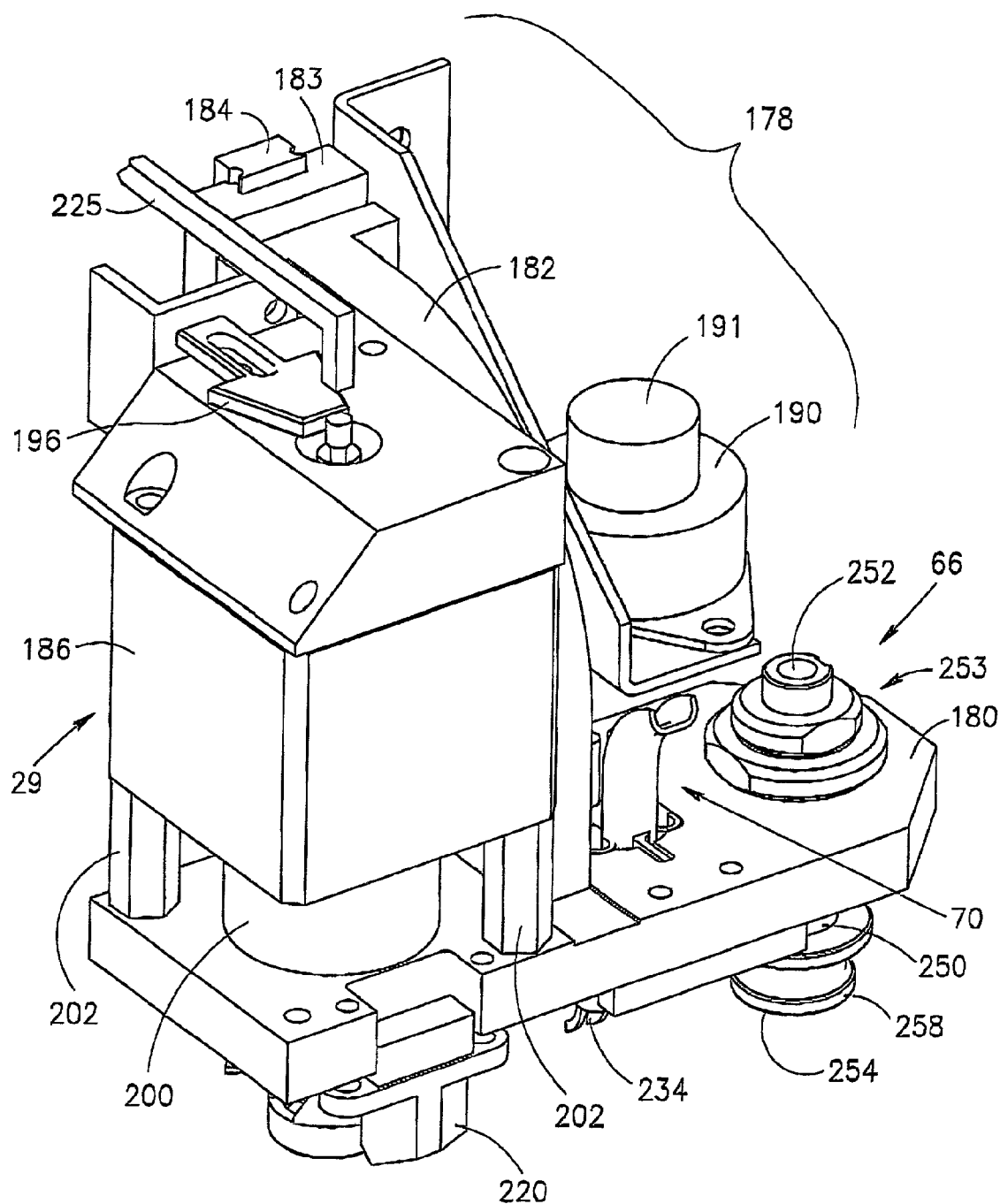
FIG. 5A is a top isometric view of the specimen handling assembly.
Figure 5B:
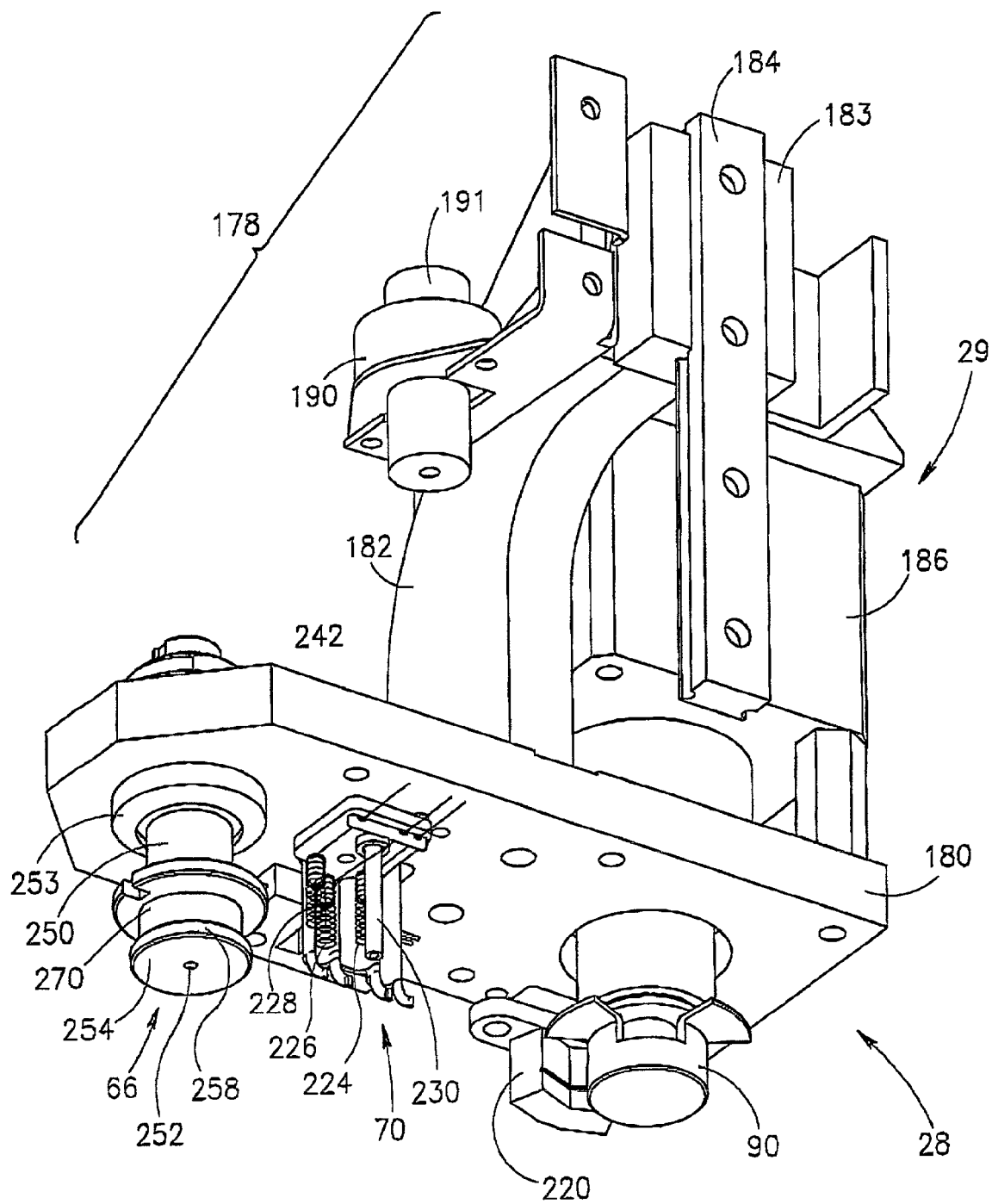
FIG. 5B is a bottom isometric view of the specimen handling assembly.
Figure 6:
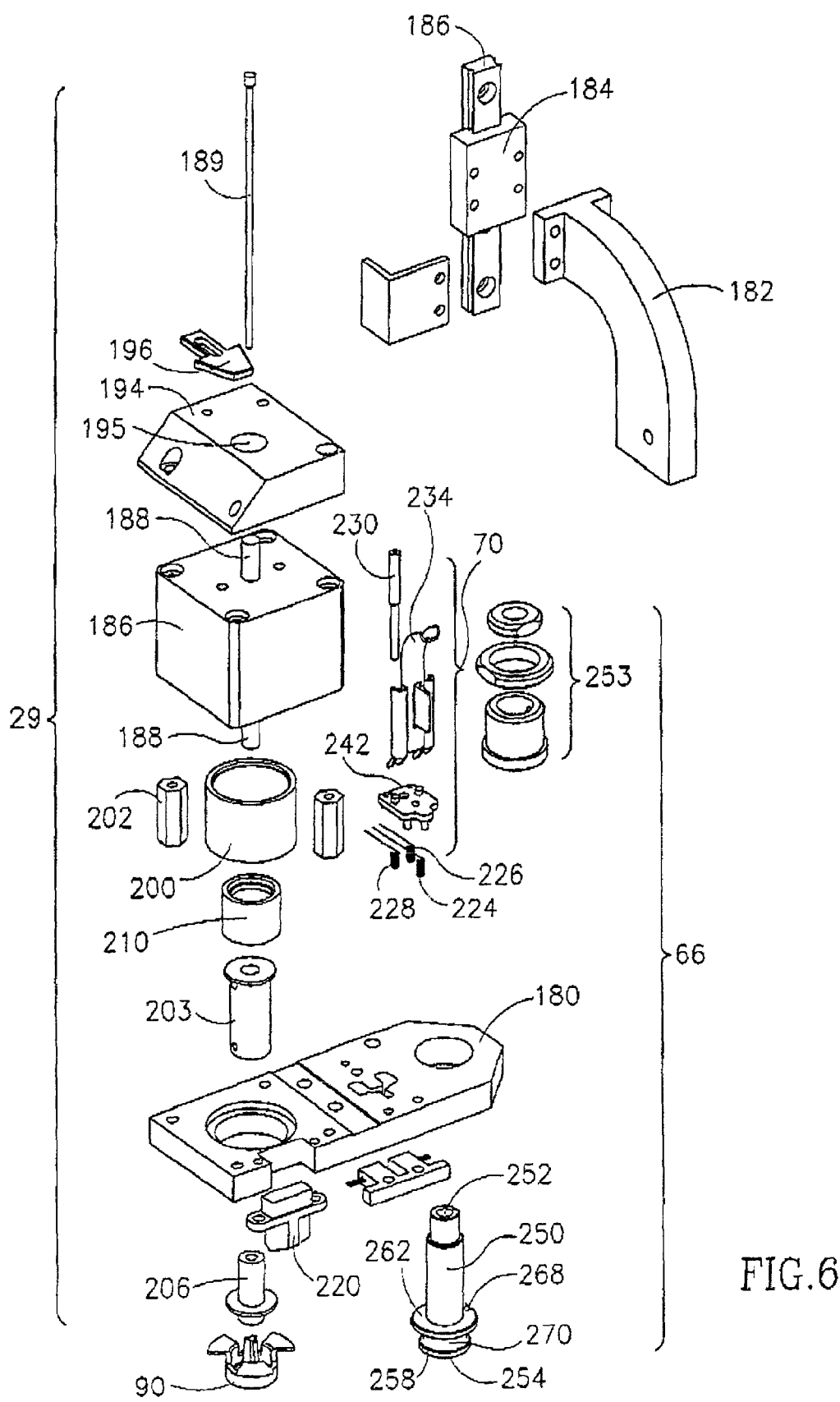
FIG. 6 is an exploded isometric view of the specimen handling assembly, namely a mixing station, dyeing and rinsing station and drying station.

For better understanding of the sub-assemblies of the specimen handling stations 28, further attention is direction to FIGS. 5A, 5B and 6, in which the three preparation stages are seen and comprising a mixing station 29, a dyeing and rinsing station 70 and a drying station 66, all mounted on a carrying platform 180 supported by an arm 182 which is fixedly attached by bolts (not shown) to a bracket 183 which in turn is slideable about a vertical profiled rail 184 which is secured to rear plate 24 of the device. Bracket 183 is slidingly articulated to rail 184 in a precise manner as known per se and is vertically displaceable thereabout by means of motor unit 190. Motor unit 190 is also connected to the controller and is fitted with an encoder 191. Alternatively, or in combination with the encoder, there may be provided one or more limit sensors (not shown).

As can best be seen in FIG. 6, the mixing station 29 comprises a motor 186 fitted with a central hollow shaft 188 through which extends a indicator pin 189 which is freely displaceable within the hollow shaft 188 between a retracted position in which it does not project from a top surface of block 194 and an extracted position in which its upper edge projects from the top surface of block 194 and is then detectable by optical sensor 196.

Figure 7:
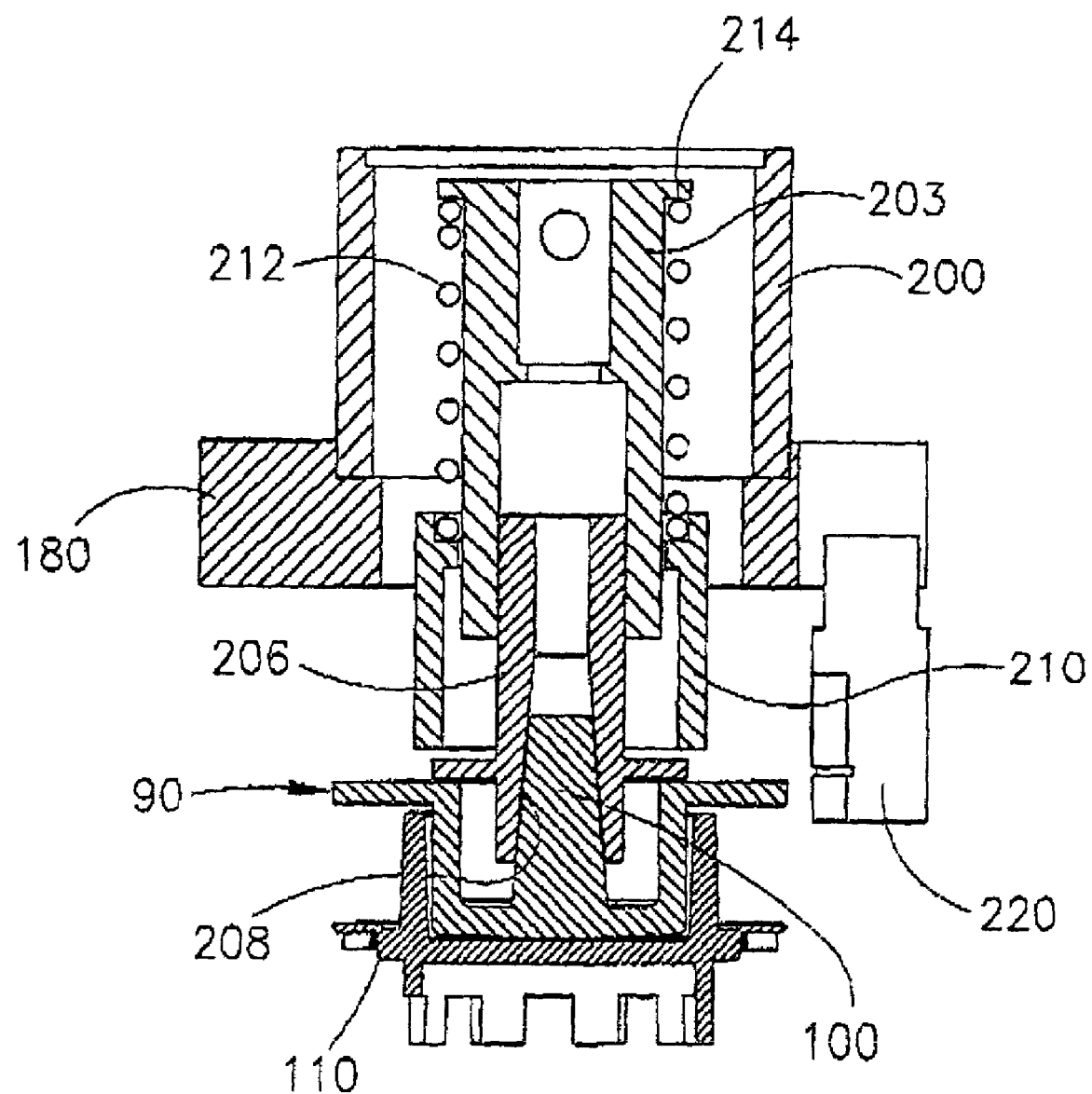
FIG. 7 is a sectional view of the cone and plate couple received within the mixing station during a mixing procedure.

With further reference also to FIG. 7, it can be seen that motor 186 is supported over a support ring 200 and the entire structure is fixed by studs 202. Received within ring 200 there is an extension sleeve 203 rotatably engaged to rotary hollow shaft 188 of motor 186. A chuck (referred to also as a collet) 206 is rotatably fixed within sleeve 203, said chuck formed at lower end thereof 208 with a tapering section adapted for friction engagement with the corresponding tapering stem member 100 of cone member 90 (FIG. 3A). Chuck 206 is received within a pressure ring 210 which is axially biased in a downward direction by means of coil spring 212 having an upper end thereof bearing against a rim 214 of sleeve 203 and at a lower end thereof bearing against an annular groove formed at ring 210. The arrangement is such that the chuck 206 is rotationally engaged with motor 186 but, on the other hand, the chuck has some axial freedom.

This arrangement provides some biasing force applied to the cone member 90 when it is engaged within chuck 206, which force gives rise to a light pressure of the cone member 90 over the plate member 110, required for proper laminate low formation procedure by the cone and plate device, as known per se.

Fitted below carrying platform 180 there is an optical sensor 220 which extends at a position such as to detect and monitor location and rotation of a cone member 90. Optical sensor 220 is fitted with an integral light source and a light detector and is capable of sensing light intermissions caused by reflection of the segmented skirt portion 96 of the cone member 90.

Articulated to rear plate 24 is an ejector arm 225 which serves to eject the cone member 90 in a manner to become apparent hereinafter.

Figure 8:
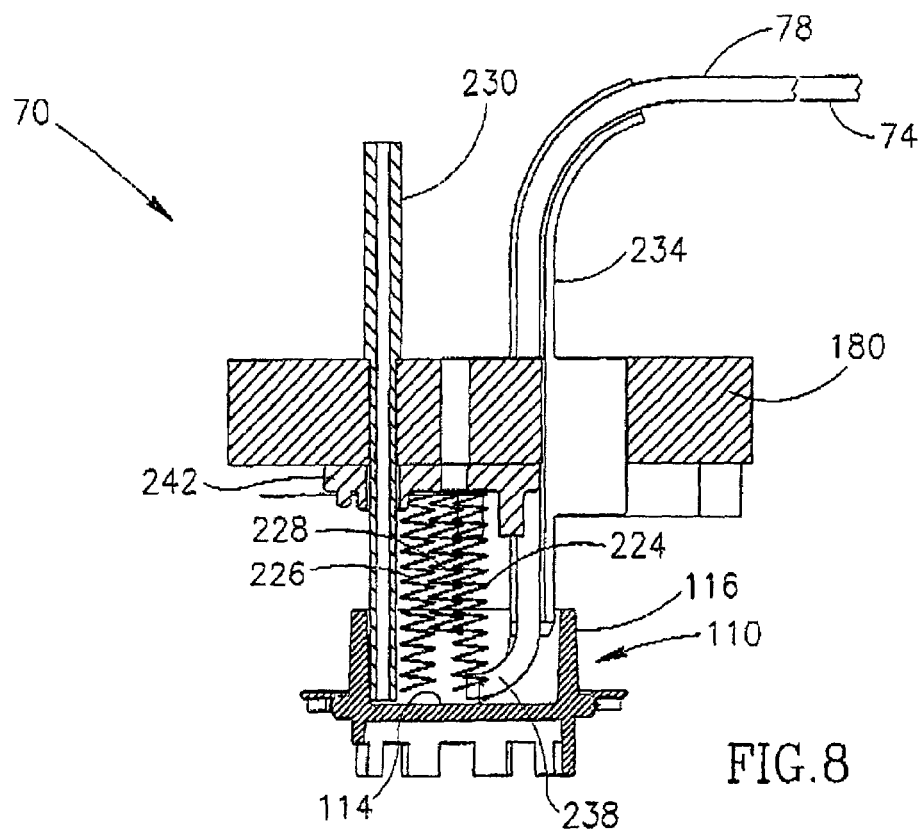
FIG. 8 is a sectional view of a plate member received at the dyeing and rinsing station.

Dyeing and rinsing station 70 (see also FIG. 8) comprises a suction pipe 230 connectable by a flexible tube 68 (see FIG. 1) to refuse vacuum container 42. Pipe 230 is rigid and at the operative suction position (see FIG. 8) it extends essentially to the bottom surface 114 of plate member 110 leaving only a clearance therefrom.

Coloring and rinsing assembly 70 further comprises a pipe holder 234 fitted for receiving flexible tube 78 extending from rinsing liquid container 46 and a second tube 74 extending from dyeing agent container 44. The arrangement is such that an end 238 of tube 78 is received within plate member 110 and it is directed so as to generate an essentially tangent flow of rinsing liquid. It is to be noted that pipe holder 234 together with the flexible tubes 74 and 78 are all disposable and typically constitute components of a diagnostic kit, as will be discussed hereinafter.

Fitted at a bottom surface of carrying platform 180 there is a liquid level sensor carrier plate 242 from which extend three coiled spring-like electrodes 224, 226 and 228 the first two of which extend downwards to a level which corresponds practically with the bottom surface 114 of plate member 110 though leaving a clearance therefrom, and the third electrode 228 extending adjacent an upper edge of the cylindrical wall portion 116 of plate member 110. The arrangement is such that electrode 224 serves as a neutral electrode whilst electrode 226 serves as a minimum liquid level sensor and electrode 228 serves as a maximum liquid level sensor by closing therebetween an electric circuit, as known per se.

Figure 9:
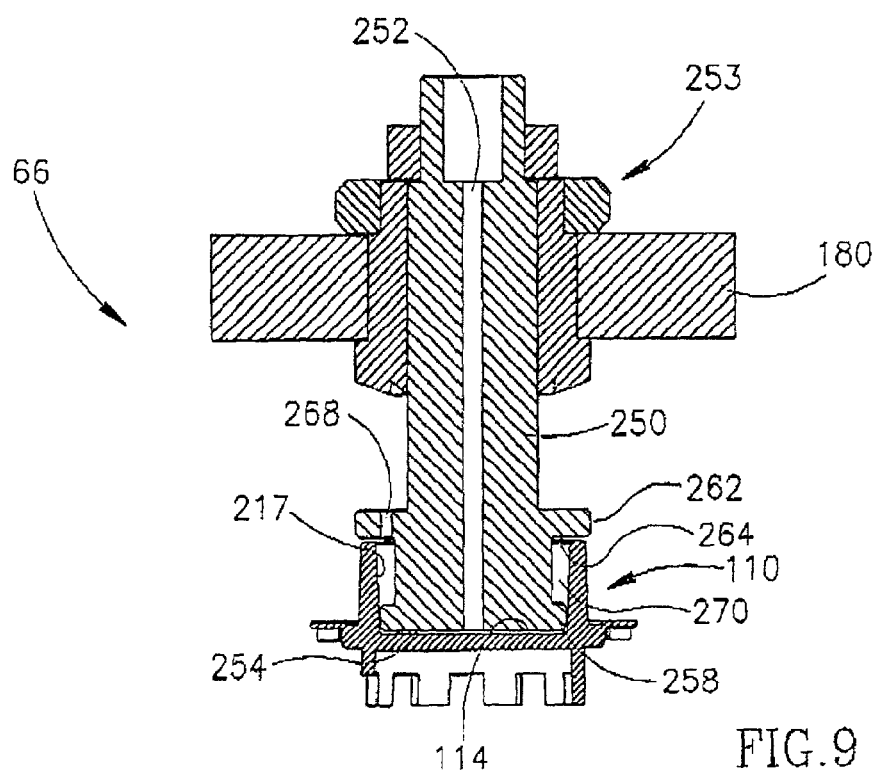
FIG. 9 is a sectional view of a plate member received at the drying station.

Further attention is now directed to the drying station 66 with further reference being made also to FIG. 9. The drying assembly comprises a plug member 250 fixedly attached to carrying platform 180 by bushings and bolts collectively designated 253. The plug 250 is connected via tube 64 (see FIG. 1) to three-way valve 60 from which tubes 58 extends to the vacuum container 42. Plug 250 is formed with a throughgoing bore 252 extending to its forehead 254 which is essentially flat. In the present embodiment bore 252 is coaxial within the cylindrical plug 250. Formed at its lower end there is a rim 258 fitted for snugly receiving within the well portion 112 of the plate member 110 (FIG. 9), however, leaving a narrow interstice between the rim 258 and the inner wall surface 117 of plate member 110.

Plug 250 is further formed with a laterally extending shoulder portion 262 having a bottom surface 264 so that in the operative position as in FIG. 9, surface 264 comes to rest over upper rim 118 of the plate member 110, thus leaving a minimal clearance between forehead 254 and surface 114 of plate member 110, the purpose of which will become apparent hereinafter.

Furthermore, the lateral shoulder is formed with at least one air inlet port 268 extending into a peripheral annular groove 270 such that when a vacuum is generated via bore 252 it gives rise to suction forces essentially all over the clearance between the forehead 254 and the surface 114, for optimal drying of the plate member 110, such that even low flow rate suction entails smearing of the droplets of liquid which together with rotation displacement of the well during a drying process, increases drying speed and efficiency.

Further attention will now be directed to FIGS. 10A to 10E for understanding how a diagnostic procedure in accordance with the present invention is carried out using a diagnostic device 20 in accordance with the present invention, in conjunction with a cone and plate couple 90 and 110, respectively.

At a first step, the system is set to an initial stage by use of the controller 39 (FIG. 1). Upon initiation of a diagnostic procedure, the system performs several self tests to determine sufficient dyeing agent in container 44, rinsing liquid in container 46, presence of a waste container 52 and to confirm that all other assemblies of the device are in order. The system will also perform a test to confirm that the service door (not shown) of a cover of the device (also not shown) is closed. Upon termination of the self tests, the carriage 32 displaces into it standby position and upon request, e.g. striking a key of the controller, the carriage displaces to the loading position, by means of motor 36, wherein receptacle 150 is accessible through the service door (not shown).

Figure 10A:
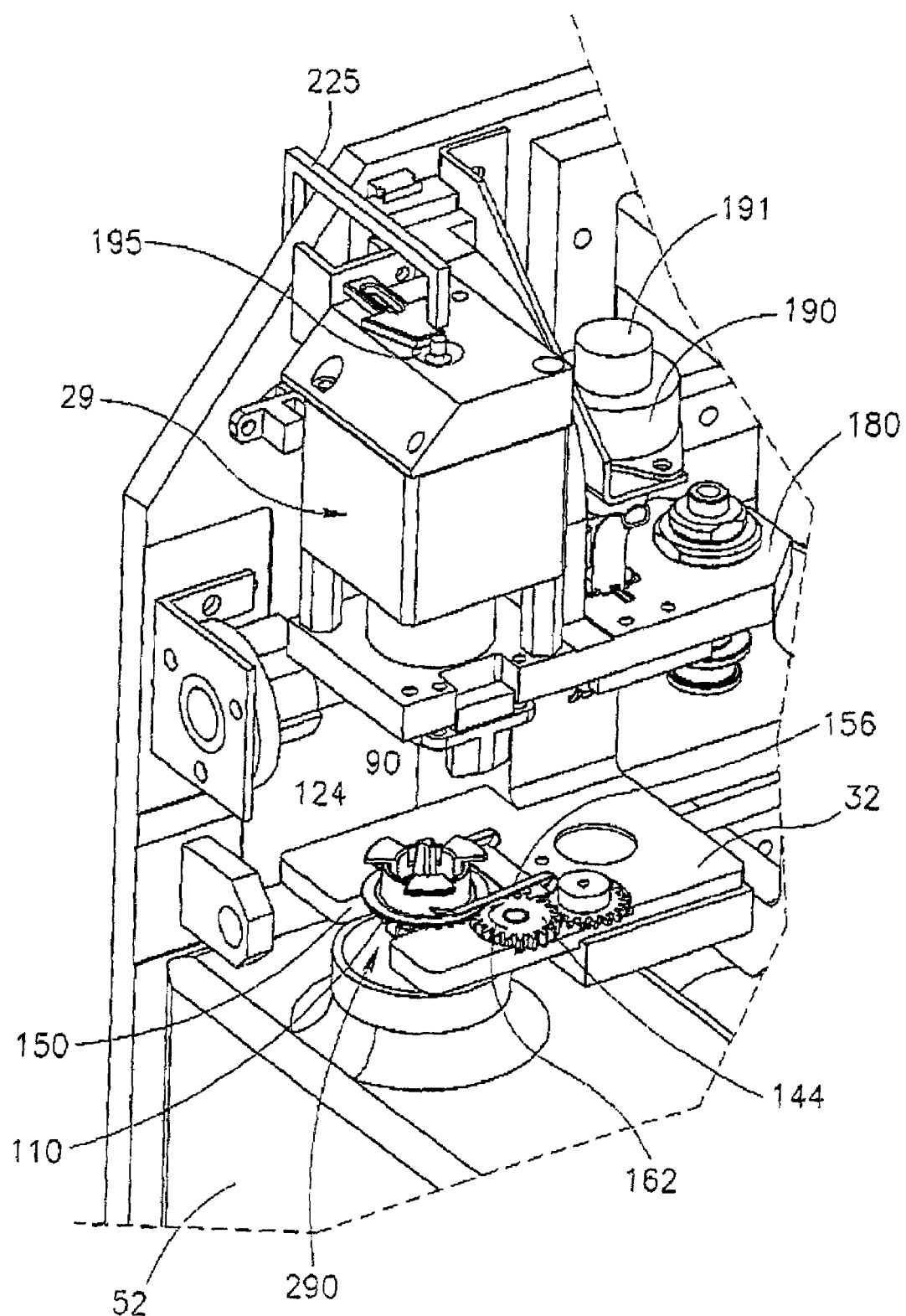
FIG. 10A illustrates a portion of the analyzing device at a first stage of loading a cone and plate couple.
Figure 10B:
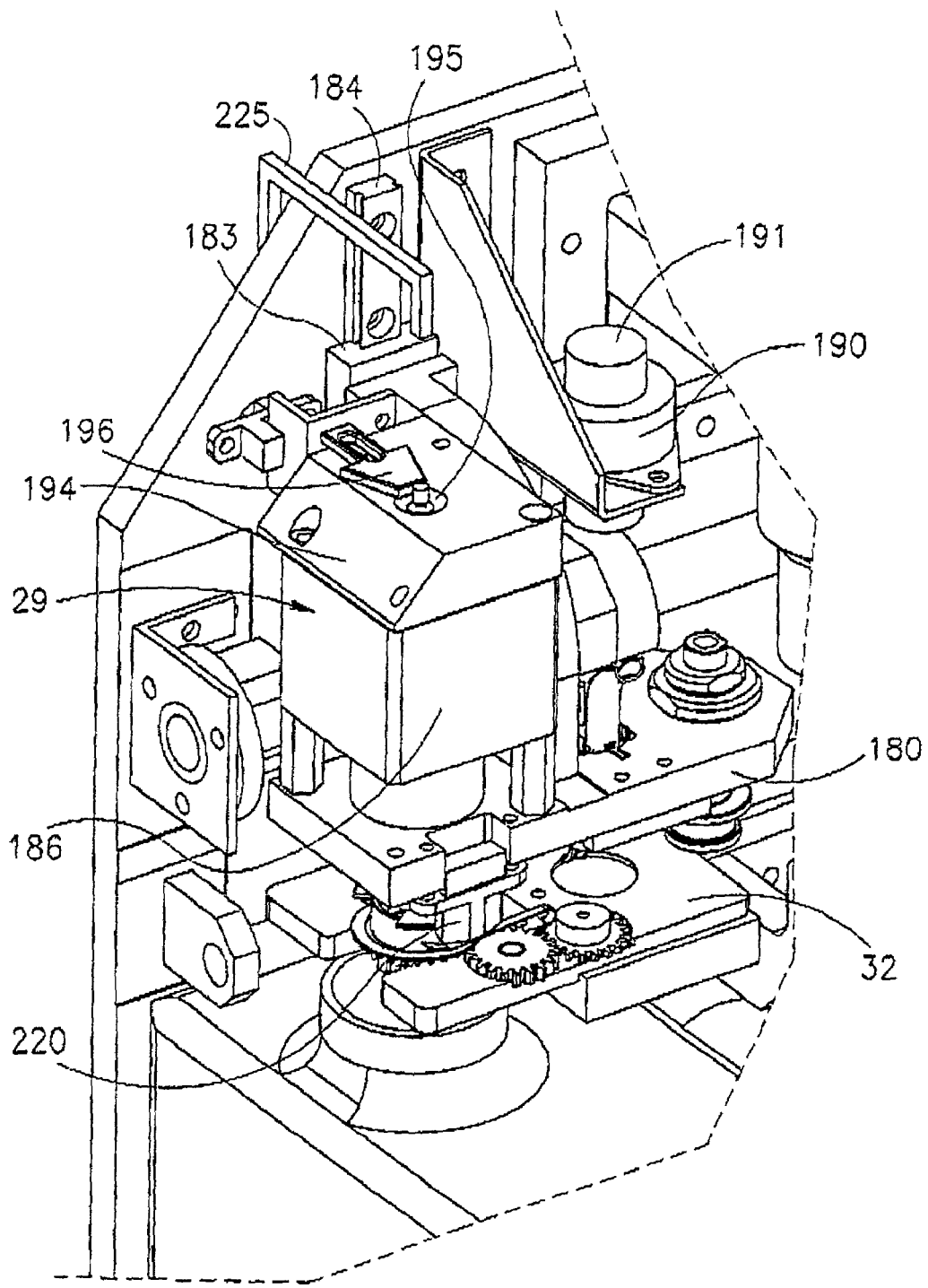
FIG. 10B illustrates a portion of the analyzing device at a cone engaging mixing stage.

A cone and plate couple 290 in their assembled position is located within the receptacle 150, as illustrated in FIG. 10A, where springy retention arms 156 bias on rim 124 of the plate member 110. Using one's finger, the cone and plate assembly 290 is pushed in as far as possible. Then, the service door is closed and the carriage 32 displaces to a position in which it extends below the mixing station 29. The controller generates a control signal to rotate transmission gear 144 in direction of arrow 162, thus confirming a true position of the cone and plate assembly 290 and testing the sensor 170 (FIG. 4A) to recognize angular displacement of the plate member 110 as explained hereinabove.

At the next step (FIG. 10B), carrying platform 180 is displaced downwards by means of electric motor 190, entailing sliding displacement of bracket 183 about profiled rail 184, to a position in which chuck 206 of mixing sub-assembly 29 engages with the stem 100 of cone member 90, as in the position of FIG. 7. Engagement of chuck 206 with the cone member 90 takes place upon axial displacement against the biasing effect of coil spring 212. Upon said engagement, the platform 180 rises to its upper position as in FIG. 10A. Optical sensor 196 extends opposite an opening 195 formed in the block 194 and the arrangement is such that when cone member 90 is engaged within the mixing sub-assembly 29, indicator pin 189 is engaged from below by the stem portion 100 of the cone member 90, resulting in that an upper end of indicator pin 189 projects through opening 195 and is then detected by sensor 196 which in turn generates a corresponding signal to the controller 39, confirming correct position of the cone member 90. If, however, the cone member is not properly engaged or in case it accidentally disengages from the chuck 206, a suitable alert signal will be generated.

Upon successful engagement of the cone member 90, the carriage 32 returns to the loading station (as in FIG. 10A) and a suitable note appears on a display panel of controller 39 (with or without a signal tone) calling for the operator to enter an identification code of the specimen and then to introduce a specimen into the well portion 112 of plate member 110. This is followed by entering a suitable command to the controller, upon which carriage 32 returns to its position below mixing sub-assembly 29, as in FIG. 10B.

Carrying platform 180 is then lowered by means of motor 190 to a position in which the cone member 90 is received within plate member 100, at a position at which the tip of the forehead of the cone member engages the base of the plate member, as illustrated in FIG. 7. Then, motor 186 is activated so as to spine the cone member 90, giving rise to mixing of the specimen. During rotation of cone member 90, sensor 220 detects and confirms rotation of the cone member 90 at a predetermined speed, so as to ensure proper engagement between the cone member and the chuck assembly of the motor. The cone member is rotated at a pre-selected speed which depends on the examined specimen and geometry of the cone and plate couple, for obtaining laminar flow profile and best shear results of the liquid specimen (typically, but not necessarily, blood) about the entire cross-section of the plate member 110, thus obtaining an essentially even smear (even distribution) of the liquid on the surface 114 of the plate member 110.

The cone member is rotated at the above speed for a predetermined period of time, determined by the examined specimen, and then the carrying platform 180 is raised, thus separating between the cone member 90 and the plate member 110. By means of sensor 196, as explained hereinabove, the controller verifies that the cone member 90 remains engaged with the mixing sub-assembly 29 and has not adhered by means of sheer force, to the plate member 110.

It was found that for blood platelet analysis the mixing stage should last about 2 minutes at a speed of about 720 RPM. For various specimens such as blood, other body cells or bacteria the mixing stage may last about 10 to 60 minutes, and the speed may vary between as slow as about 50 RPM to as fast as about 30,000 RPM.

At this state, the specimen is essentially evenly smeared on the surface 114 of the plate member 110. The carriage 32 then displaces to the position seen in FIG. 10F, in which the plate member 110 reaches the imaging station 30, comprising a microscope 300 and an image capturing device 302, typically a digital camera. At this situation the LED light source 301 is activated and the system scans the surface 114 of plate member 110, to determine significant light transparency through the transparent or translucent base surface 114 of the plate member, resulting due to coverage of the surface by blood. This step confirms that the specimen has indeed been introduced into the plate member 90.

Figure 10C:
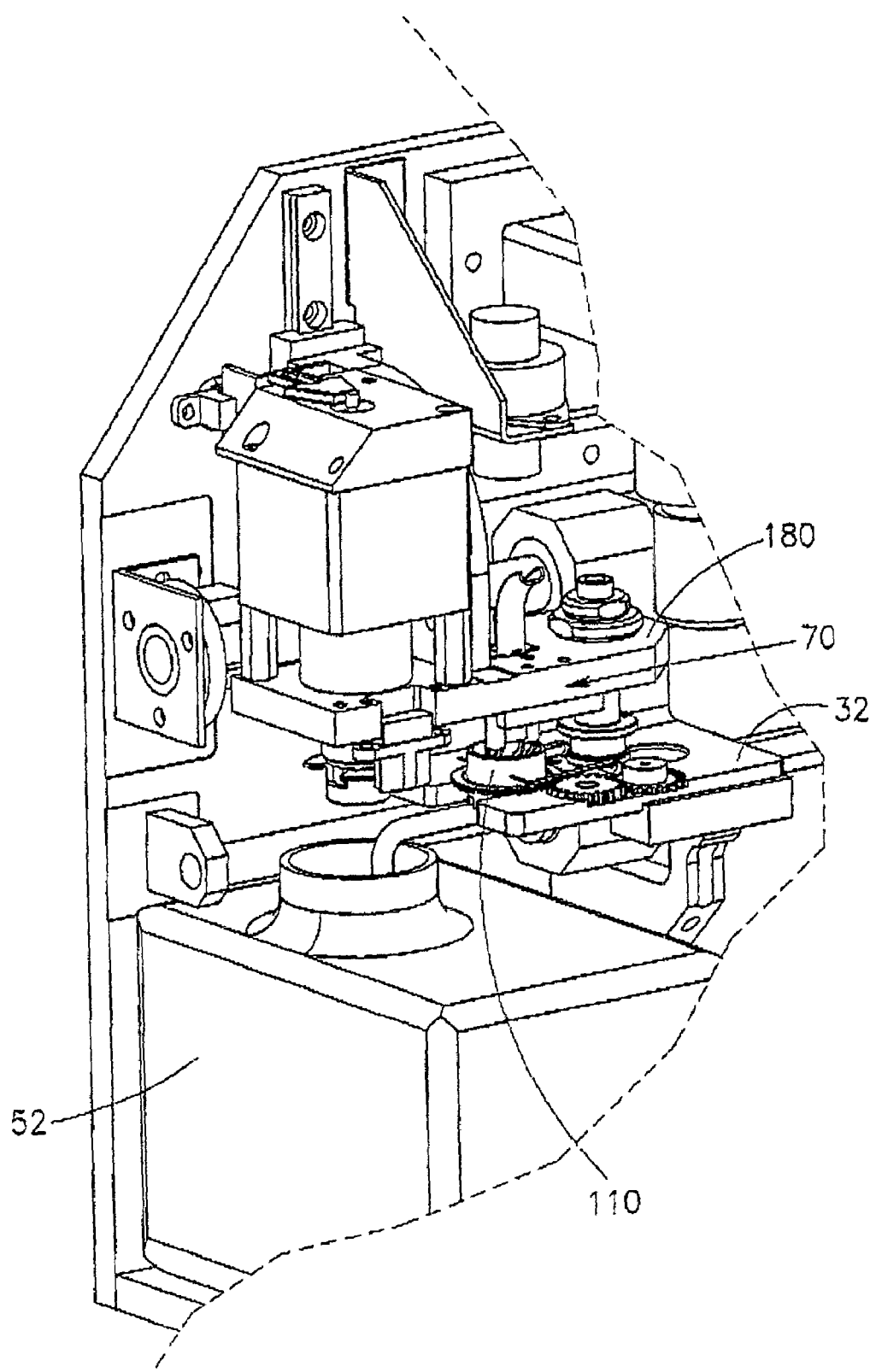
FIG. 10C illustrates a portion of the analyzing device with the carriage at the dyeing and rinsing station during a dyeing or rinsing stage.
Figure 10D:
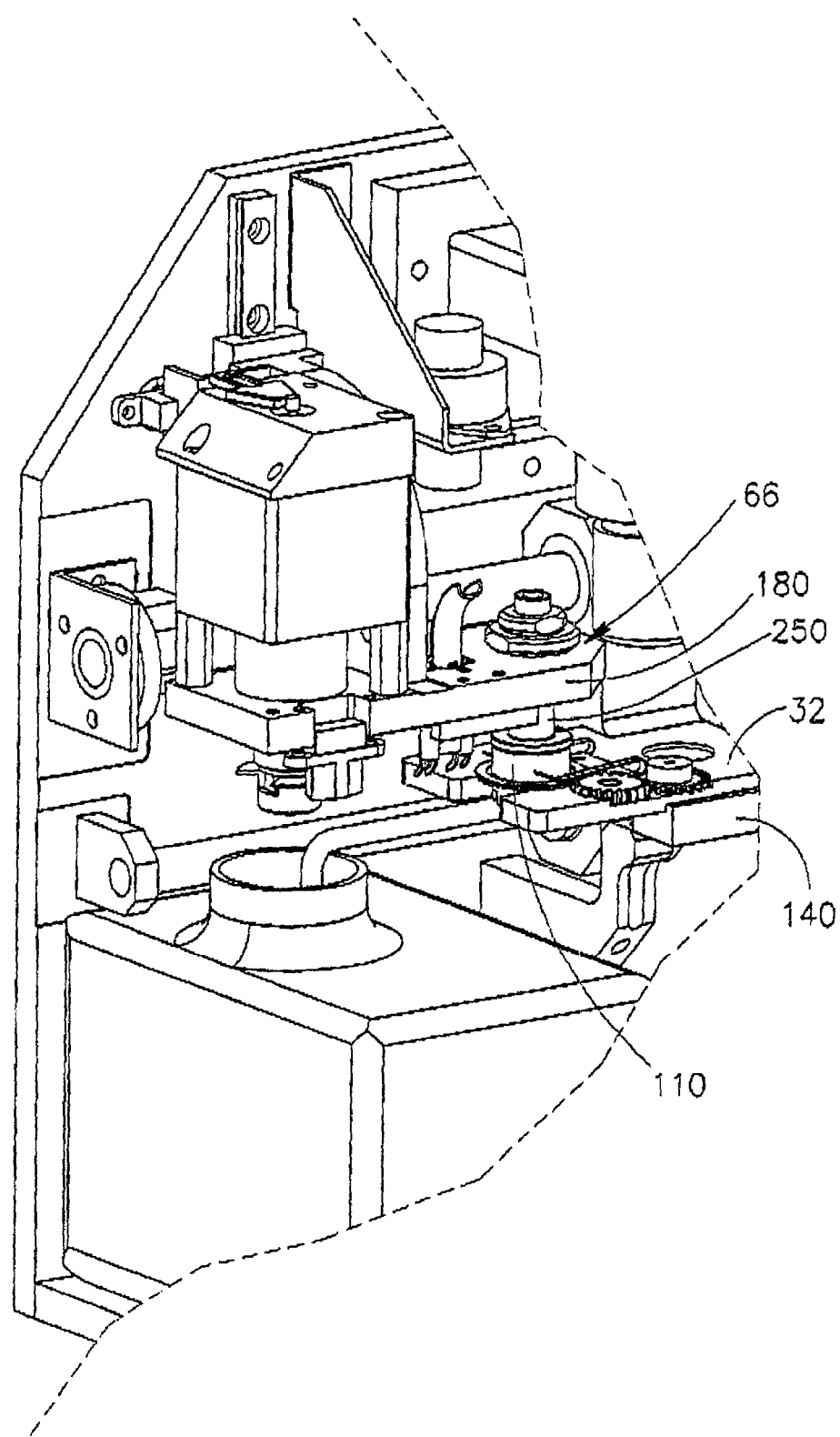
FIG. 10D illustrates a portion of the analyzing device with the carriage at the drying station during a drying stage.
Figure 10E:
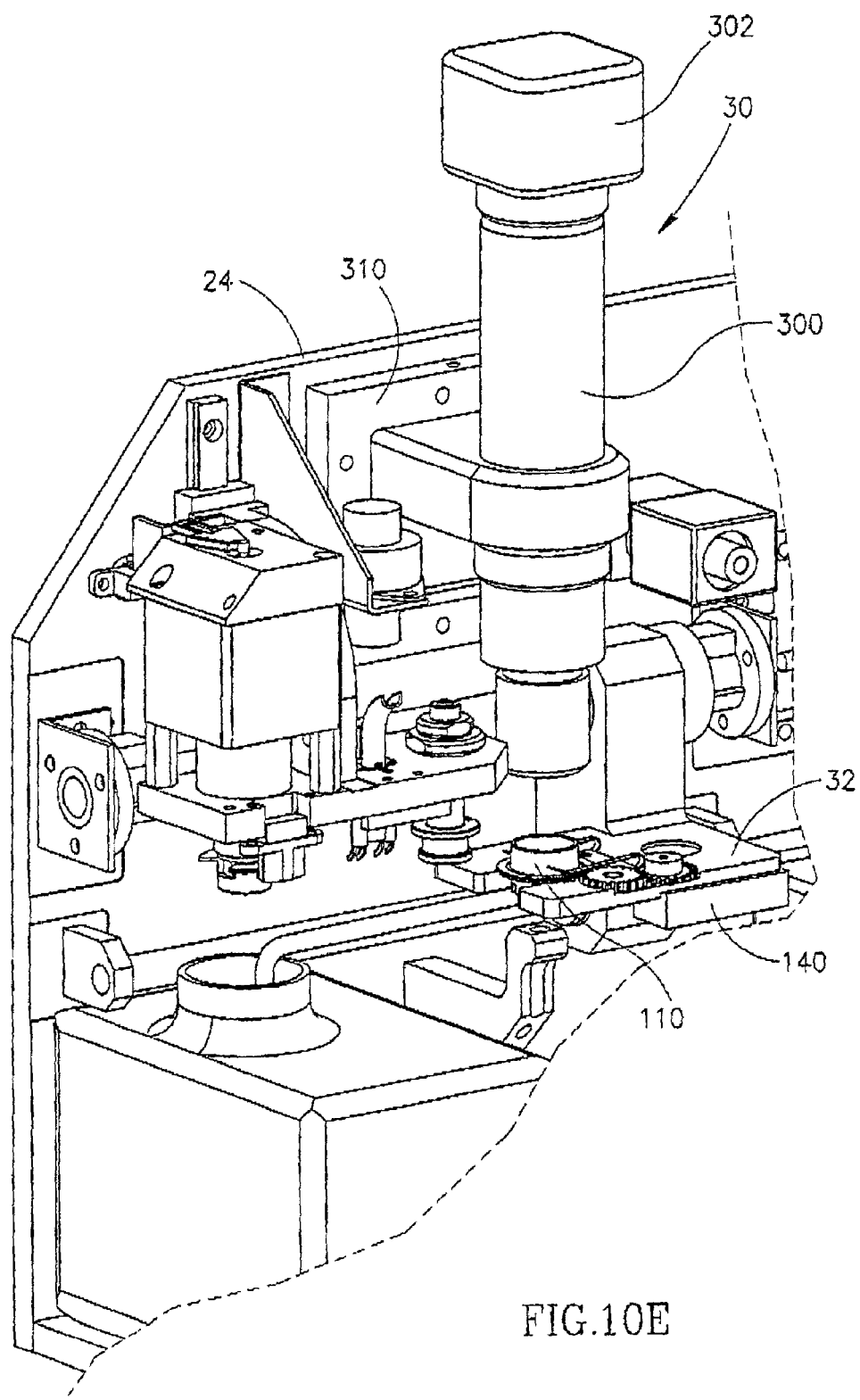
FIG. 10E illustrates a portion of the analyzing device with the carriage at the imaging station.

From the imaging station 30, carriage 30 returns to the dyeing and rinsing sub-assembly 70 (FIG. 10C). Carrying platform 180 then descends to a dyeing and rinsing operative level as in FIG. 8. Then, peristaltic pump 50 is activated with a rinsing liquid flushing well 112 of plate member 110, whereby simultaneously vacuum pump (FIG. 1) is activated, giving rise to vacuum built up within vacuum container 42. It is pointed out that at this stage the three way valve 60 is set such that it is directed to the drying sub-assembly 66, i.e. at this stage there is no suction from the dyeing and rinsing station 70.

By means of electrodes 224, 226 and 228 (FIGS. 5B, 6 and 8), the controller determines the level of rinsing liquid within the well 112 of plate member 110, until the well 112 is filled at a predetermined level. Then, after a short delay, the three way valve 60 is opened so as to give rise to suction of the liquid from the plate member 110 through pipe 230 and then via tube 68 into vacuum container 42.

This rinsing procedure takes place several times (e.g. 6–8 times), and then a similar procedure takes place, though this time instead of introducing rinsing liquid, a dyeing agent is propelled from container 44 via tube 74 into the well 112 of plate member 110, by means of peristaltic pump 48. This procedure takes place several times, typically twice and after the last dyeing procedure, the dyeing agent remains in the plate member 110 and the carrying platform 180 ascends, allowing the carriage 32 to displace to the drying station 66 as in FIG. 10D.

As the carriage 32 reaches the drying station 66, the three way valve 60 is shifted into a so-called drying state in which vacuum through tube 58 and then tube 64 is applied to the plug 250, whilst the motor 140 rotates the plate member 110. Rotation of plate member 110 is confirmed by means of optical sensor 170 (FIG. 4A) as discussed hereinabove. The drying procedure takes place by applying a low flow rate suction through the plug 250, which owing to the tight clearance between the corresponding surfaces of the plug and the surfaces of the well portion 112 of plate member 110, cause smearing of the liquid droplets and their drying of the surface 114.

After a predetermined period of time in which the plate member 110 is assumed to be dry, the motor 140 and the vacuum pump 40 are stopped ceased and then carrying platform 180 raises so as to disengage the drying assembly from the plate member. The carriage 32 is displaced to the imaging station 30 as in FIG. 10E and the three-way valve 61 is then opened to admit free liquid flow from vacuum container 42 to waste container 52.

In the present embodiment, the imaging device is a microscope 300, with LED illumination source 301 bellow the carriage and it is fixed to the rear plate 24 by means of mounting bracket 310. However, the arrangement is such that as the carriage 32 reaches the imaging station, as in FIG. 10E, the object of the microscope 300 extends offset with respect to an axis of the plate member 110. Preferably, but not necessarily, the object of the microscope axially extends at about midway of the ruddy of the base surface 114 of plate member 110.

The controller then generates several consecutive signals giving rise to intermittent angular displacement of plate member 110 by means of motor 140. Each time the motor stops, a corresponding signal is issued to image capturing device 320 to capture an image via the microscope 300. In this manner, statistical image sampling of the preparation is obtained, as may be required.

However, it should be obvious to a person versed in the art that rather then angular displacement, the plate member or the imaging device may be displaced about an X-Y coordinate system, or about a polar coordinate system, whereby several consecutive images are obtained for reaching statistical analyses of the preparation.

Figure 11A:
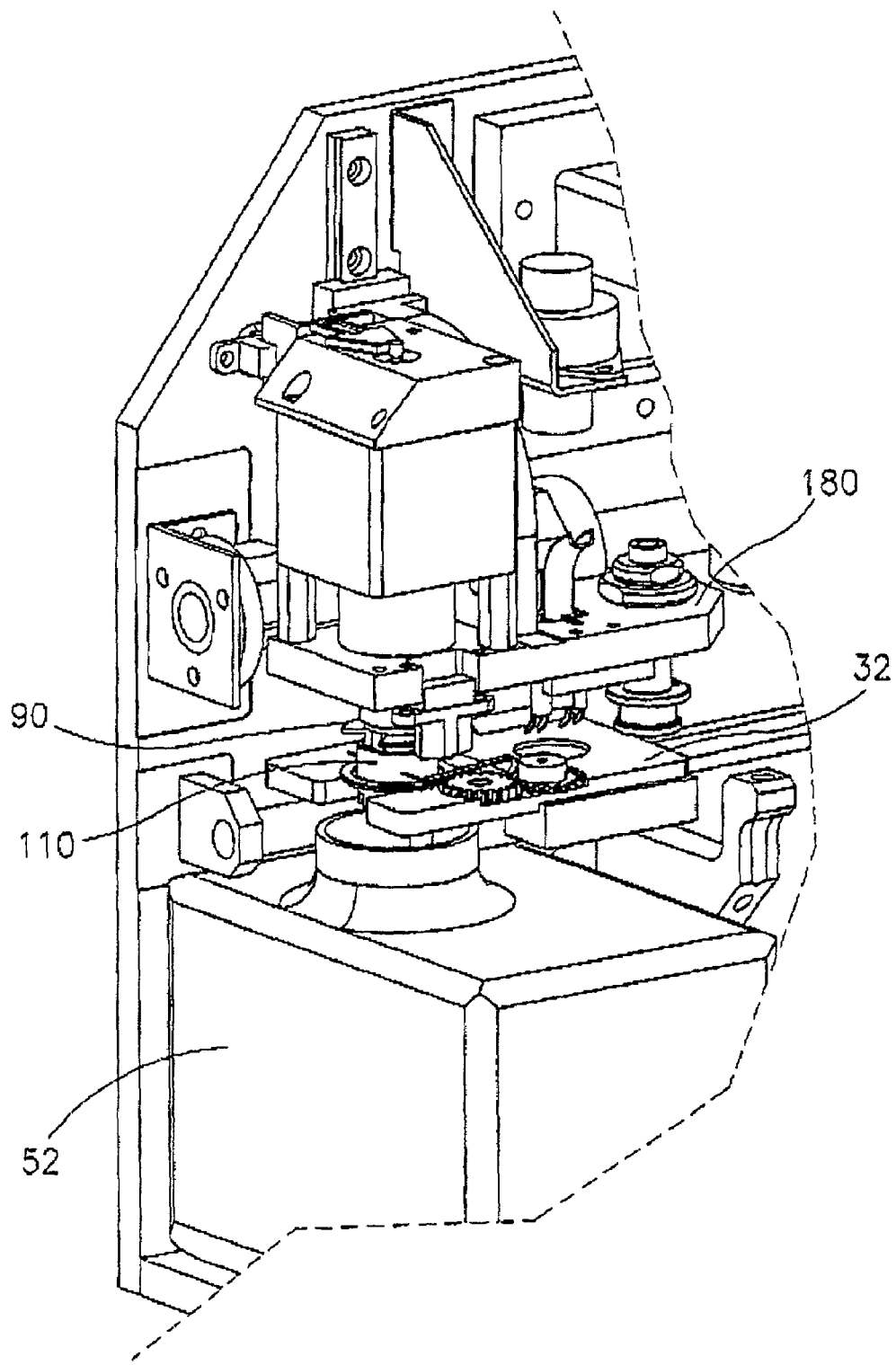
FIG. 11A illustrates the analyzing device at a first stage of unloading and disposing of a plate member.
Figure 11B:
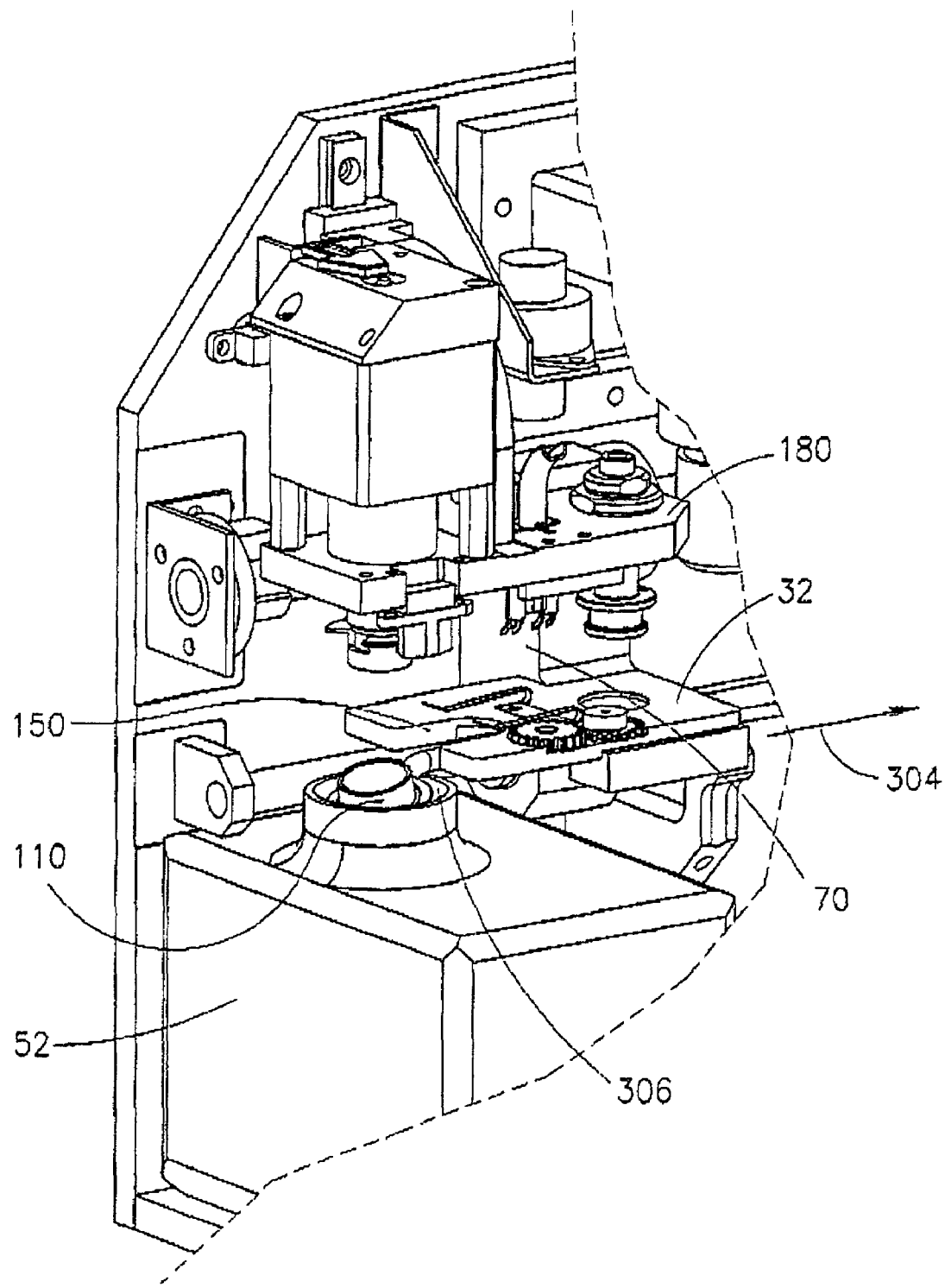
FIG. 11B illustrates the analyzing device at a second stage of disposing the plate member.
Figure 11C:
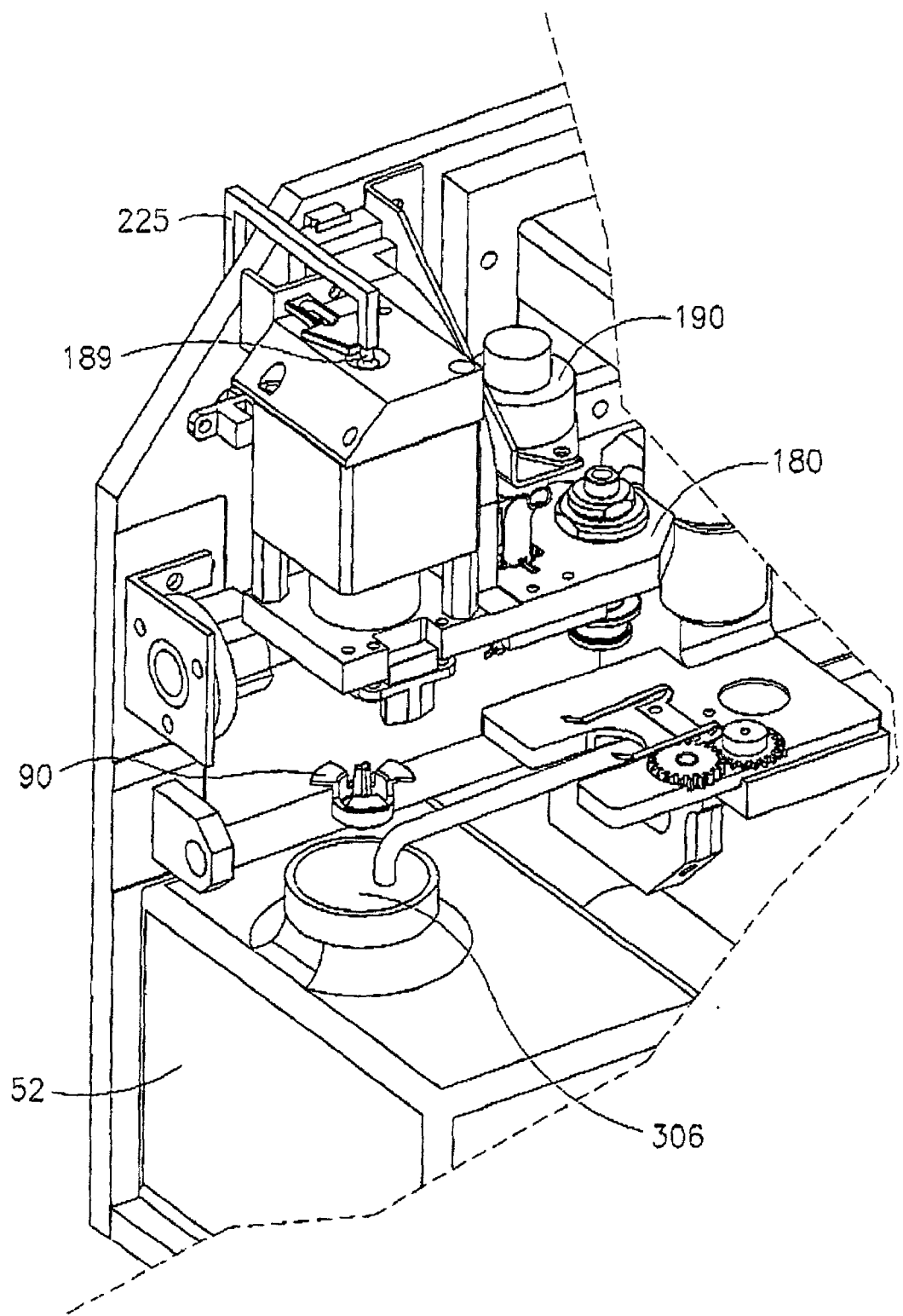
FIG. 11C illustrates the unloading and disposing of a cone member.

Upon completion of the image sampling process, carriage 32 displaces to an unloading position (FIG. 11A) wherein carrying platform 180 is lowered to a position in which the cone member 90 is at least partially engaged within plate member 110 and then the carriage 32 displaces in a direction of arrow 304, towards the dyeing and rinsing assembly 70 (FIG. 11B) giving rise to disengagement of the plate member from the receptacle 150 of carriage 32, allowing it to fall into waste container 52 via its aperture 306.

Then, the carrying platform 180 is elevated by means of motor 190 until a position in which an upper end of indicator pin 189 engages the ejector arm 225 resulting in axially displacing of the cone member 90, disengaging it from the chuck assembly and allowing it to fall into waste container 52 via opening 306.

At this state, the controller sets the system to a standby position allowing data to be processed by a suitable processor to display and print the analysis results. The controller will simultaneously perform tests to determine sufficient liquid level in the liquid containers, determining that the waste container 52 is not full, etc.

A dyeing agent may sometimes dry and clog the tubes. Accordingly, it is advantageous to replace periodically some of the components.

It is in accordance with a further aspect to provide a kit for use with a diagnostic device in accordance with the present invention. Such a kit will typically comprise several cone and plate couples together with replacement flexible tubes, waste container 52 and fresh liquid containers (dyeing agent container 44 and rinsing liquid container 46). Where a printer is provided for printing the analysis results the kit may include also an ink cartridge for the printer, as well as a supply of paper.

The controller may have several pre-programmed or programmable functions, setting as an example a timer which if detecting a lapse between one analysis and a consecutive analysis, say more than 15 minutes, the peristaltic pumps 48 and 50 operate in a reverse direction so as to propel the dyeing agent and rinsing liquid into their respective containers 44 and 46, to prevent clogging of the piping. In such a case, upon reactivation of the system, suitable measures have to be taken to propel sufficient liquid into the system upon deactivation thereof.

In order to prevent usage of non-genuine disposable components, in particular a cone and plate couple, the plate member 110 may be provided with some sort of encoding which may be detectable by the imaging system. Such encoding may either be a complicated printed pattern or other sort of encryption which only upon identification by the imaging system and certification by the controller, the device will perform an analysis. Such an encryption may be, for example, imparting a pattern on the base surface 114 on plate member 110, which pattern will have to be recognized by the optical system.

What is claimed is:

1. A device for analyzing liquid body-specimens, the device comprising:

at least one specimen handling station for obtaining a preparation containing a body-specimen on a carrying media, said carrying media comprising a plate member having a surface;

a mixing station for smearing the body-specimen on said surface;

an imaging station fitted with an optical image capturing device for analyzing the preparation;

a carriage fitted with a carrying media receptacle adapted for retaining therein the carrying media and being displaceable at least between a loading position, in which said carrying media receptacle engages the specimen handling station, a mixing position in which carrying media receptacle is located at said mixing station, an imaging position in which said carrying media receptacle is located at said imaging station, and an unloading position, in which said carrying media receptacle disengages the specimen handling station;

a programmable controller; and an incremental displacement mechanism configured for effecting relative displacement between said carrying media receptacle and the image capturing device while said carrying media receptacle is located at said imaging station, said relative displacement being such as to permit said optical image capturing device to selectively obtain consecutive images of two or more different locations of said preparation on said surface, the locations being defined by said relative displacement.

2. An analyzing device according to claim 1, wherein either one of the carrying media and the imaging device is incrementally displaceable about an X-Y coordinate system or a polar coordinate system or is angularly displaceable.

3. An analyzing device according to claim 1, wherein the at least one handling station comprises said mixing station, incorporating a mixer/shaker mechanism, a coloring stage, a rinsing stage and a drying stage.

4. An analyzing device according to claim 3, wherein the at least one handling station comprises at least one container holding a preparation liquid, and the device further comprises a waste container for collecting refuse liquids and carrying media and fluid pump arrangements for propelling fluids between stations.

5. An analyzing device according to claim 1, wherein the carrying media is a well composed of a plate member, and a cone member cooperating with said plate member, whereby the well is rotatably engageable with the carriage receptacle and wherein at the mixing station the cone member is rotatable within the plate member.

6. An analyzing device according to claim 5, wherein the plate member is displaceable within the carriage receptacle at angular increments.

7. An analyzing device according to claim 5, wherein at the mixing station the well is retained fixed while the cone member is rotatably engaged within the well.

8. An analyzing device according to claim 5, wherein the mixing station comprises a housing fitted with a rotary motor and being axially displaceable for respectively introducing and removing the cone member from the plate member.

9. An analyzing device according to claim 4, further comprising an air pressure/vacuum source for suction of refuse liquids from the carrying media and for drying at the drying stage.

10. An analyzing device according to claim 1, wherein the imaging station comprises a microscope and a camera for capturing images of the preparation, with an objective of the microscope extending offset with respect to the carrying media.

11. An analyzing device according to claim 10, wherein the microscope is fitted with a LED-type illumination source.

12. A device for analyzing liquid body-specimens, the device comprising
at least one specimen handling station for obtaining preparation on a carrying media comprising a well, and an imaging station on fitted with an optical image capturing device for analyzing the preparation;
a carriage fitted with a carrying media receptacle retaining the carrying media and being displaceable between a loading position and an unloading position with respective positions at said stations;
a programmable controller; and
an incremental displacement mechanism for displacing at least one of said carrying media and an imaging device so as to obtain at least one consecutive image of the preparation,
wherein the at least one handling station comprises a mixer/shaker mechanism, a coloring stage, a rinsing stage and a drying station,
wherein the drying station comprises a cylindrical plug insertable into the well with a forehead of the plug being essentially flat and having a diameter snugly receivable within the well; at least one air suction port formed at the forehead and a suitable venting inlet to admit air flow towards the forehead; the plug further comprising an axial restriction arrangement for obtaining a fixed clearance between the forehead and a base of the well.

13. An analyzing device according to claim 12, wherein the plug is formed with a peripheral air channel extending above the forehead, and being in flow communication with the venting inlet.

14. An analyzing device according to claim 12, wherein the axial restricting arrangement comprises a shoulder of the plug engageable with a corresponding seat portion formed at a peripheral wall of the well.

15. An analyzing device according to claim 1, wherein the carrying media is fitted with indicia for communicating with a corresponding sensing arrangement, for detecting and monitoring rotary motion thereof.

16. An analyzing device according to claim 5, wherein the well and cone member are each fitted with indicia for communicating with corresponding sensors, for detecting and monitoring rotary motion thereof.

17. An analyzing device according to claim 3, wherein the coloring and rinsing stages comprise a liquid introducing and withdrawal tubing and a liquid-level sensing mechanism.

18. An analyzing device according to claim 17, wherein the liquid introducing tubing is formed so as to direct liquid flow at an essentially tangent direction within the well.

19. An analyzing device according to claim 17, wherein the liquid-level sensing mechanism comprises three spring-like electrodes, two of which extend proximal to the base of the well, and one at a maximum liquid level.

20. An analyzing device according to claim 1, further comprising control valving for selectively directing fluid flow between the various stations.

21. An analyzing device according to claim 4, wherein the fluid pump arrangements comprises an air pressure/vacuum generator and one or more peristaltic pumps for propelling liquids.

22. An analyzing device according to claim 8, wherein optical sensors are provided for detecting and monitoring rotation of the well with respect the carriage and of the cone member with respect the housing of the mixing station.

23. An analyzing device according to claim 8, wherein the mixing station comprises a chuck for releasable engagement with a stem coaxially extending from the cone member.

24. An analyzing device according to claim 23, wherein the stem of the cone member has a tapering cross-section corresponding with a conical cross-station of the chuck.

25. An analyzing device according to claim 5, wherein the well is formed with a substantially flat and smooth surface with a cylindrical wall upwardly extending therefrom, with en engagement portion for engaging with a rotary motor of the carriage.

26. An analyzing device according to claim 25, wherein a bottom portion of the well is formed with a geared path for engagement with a corresponding geared transmission of a rotary motor fitted in the carriage.

27. An analyzing device according to claim 25, wherein the well further comprises a skirt formed with one or more recesses for association with an optical sensor detecting and monitoring rotation of the well.

28. An analyzing device according to claim 26, wherein the geared path is concealed by a skirt portion laterally extending beyond the geared path.

29. An analyzing device according to claim 28, wherein the skirt portion is essentially parallel to the base surface of the plate member.

30. An analyzing device according to claim 1, wherein security arrangements are provided for identifying the carrying media and certifying its matching with the analyzing device.

31. An analyzing device according to claim 30, wherein the carrying media is fitted with an encryption detectable by the imaging device.

32. An analyzing device according to claim 5, wherein the carriage is fitted with a well receptacle and a motor for imparting rotary motion to the well, and arresting members for engaging the well at an operative position within the receptacle.

33. An analyzing device according to claim 5, wherein the receptacle of the carriage has a U-like shape, wherein the arm extensions constitute a feeding opening for the well and at an operative position the well is positioned snugly at the circular portion of the receptacle; and the carriage comprises a driving gear for engagement with a corresponding geared path of the well, said driving gear extending offset with respect a longitudinal axis of the receptacle.

34. A method for analyzing liquid body-specimens, the method comprising the following steps:
(a) obtaining a liquid body-specimen analyzer comprising at least one specimen handling station for obtaining a preparation on a surface of a carrying media, an imaging station fitted with an optical image capturing device, a carriage fitted with a carrying media receptacle and being displaceable between a loading position, and an unloading position with respective positions at said stations, and a programmable controller;
(b) engaging the specimen carrying media with the carriage;
(c) obtaining a specimen of body liquid and introducing the specimen on the surface of the carrying media;
(d) smearing the specimen substantially uniformly over the surface;

(e) displacing the carriage from the loading position to the at least one specimen handling station so as to obtain a preparation on the surface;
(f) advancing the carriage to the imaging station and effecting relative displacement between the carrying media and the image capturing device while the carrying media is located a the imaging station for obtaining consecutive images of two or more different locations of the preparation on said surface, the locations being defined by the relative displacement; and
(g) displacing the carriage to the unloading position for disposal of the carrying media.

35. An analyzing method according to claim 34, wherein during or after step (e) refuse agents used at the at least one specimen handling station are disposed to a waste container.

36. An analyzing method according to claim 34, wherein the carrying media is a plate and cone couple.

37. An analyzing method according to claim 36, wherein at the handling station of step (e) the plate is retained stationary and the cone is rotated against the plate member for mixing the specimen.

38. An analyzing method according to claim 37, wherein after mixing the specimen is colored and then dried.

39. An analyzing method according to claim 36, wherein at step (f) the plate is rotated in increments so as to obtain a plurality of images of the preparation, said images being captured by the optical image capturing device.

40. An analyzing method according to claim 34, wherein at step (f) the plate member is incrementally angularly displaced.

41. An analyzing device according to claim 8, wherein said rotary motor provides relative rotational movement between said cone member and said plate member such as to generate laminar flow of a preparation on said surface.

42. An analyzing device according to claim 8, wherein said rotary motor provides relative rotational movement between said cone member and said plate member such as to smear said preparation substantially evenly on said surface.

* * * * *

UNITED STATES PATENT AND TRADEMARK OFFICE
CERTIFICATE OF CORRECTION

PATENT NO. : 6,989,272 B1  
APPLICATION NO. : 09/799355  
DATED : January 24, 2006  
INVENTOR(S) : Naphtali Savion and Doron Lindner It is certified that error appears in the above-identified patent and that said Letters Patent is hereby corrected as shown below:

Column 13, line 11 (Claim 12, line 5), after "station," delete "on"  
Column 13, line 31 (Claim 12, line 25), delete "restriction" and insert therefor - -restricting- -  
Column 15, line 7 (Claim 34, subparagraph (f), line 5), after "located," delete "a" and insert therefor - -an- -

Signed and Sealed this

Fifteenth Day of August, 2006

JON W. DUDAS  
*Director of the United States Patent and Trademark Office*

UNITED STATES PATENT AND TRADEMARK OFFICE
CERTIFICATE OF CORRECTION

PATENT NO. : 6,989,272 B1 Page 1 of 1
APPLICATION NO. : 09/799355
DATED : January 24, 2006
INVENTOR(S) : Savion et al.

It is certified that error appears in the above-identified patent and that said Letters Patent is hereby corrected as shown below:

Column 15, line 7 (Claim 34, subparagraph (f), line 5), after "located," delete "a" and insert therefor --at--

Signed and Sealed this

Fourteenth Day of August, 2007

JON W. DUDAS
*Director of the United States Patent and Trademark Office*